United States Patent
Benmoussa et al.

(10) Patent No.: US 12,365,709 B2
(45) Date of Patent: *Jul. 22, 2025

(54) IMMUNOMODULATORY PEPTIDE

(71) Applicants: INSTITUT NATIONAL UNIVERSITAIRE JEAN-FRANCOIS CHAMPOLLION, Albi (FR); UNIVERSITE TOULOUSE III—PAUL SABATIER, Toulouse (FR); INSTITUT NATIONAL DE LA SANTE ET DE LA RECHERCHE MEDICALE, Paris (FR); UNIVERSITE DE ROUEN-NORMANDIE, Mont Saint Aignan (FR)

(72) Inventors: Khaddouj Benmoussa, Ramonville Saint Agne (FR); Elsa Bonnafe, Albi (FR); Agnès Coste, Blagnac (FR); Jérôme Leprince, Mont Saint Aignan (FR); Bernard Pipy, Toulouse (FR); Michel Treilhou, Lescure-d'Albigeois (FR)

(73) Assignees: INSTITUT NATIONAL UNIVERSITAIRE JEAN-FRANCOIS CHAMPOLLION, Albi (FR); UNIVERSITE TOULOUSE III—PAUL SABATIER, Toulouse (FR); INSTITUT NATIONAL DE LA SANTE ET DE LA RECHERCHE MEDICALE, Paris (FR); UNIVERSITE DE ROUEN-NORMANDIE, Mont Saint Aignan (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/364,665

(22) Filed: Aug. 3, 2023

(65) Prior Publication Data
US 2024/0101618 A1 Mar. 28, 2024

Related U.S. Application Data

(63) Continuation of application No. 16/476,788, filed as application No. PCT/FR2018/050072 on Jan. 12, 2018, now Pat. No. 11,753,452.

(30) Foreign Application Priority Data

Jan. 12, 2017 (FR) .................................. 1750280

(51) Int. Cl.
| | | |
|---|---|---|
| A61K 38/00 | (2006.01) |
| A61P 31/10 | (2006.01) |
| A61P 35/00 | (2006.01) |
| C07K 5/08 | (2006.01) |
| C07K 5/10 | (2006.01) |
| C07K 7/06 | (2006.01) |
| C07K 7/08 | (2006.01) |
| C07K 14/435 | (2006.01) |

(52) U.S. Cl.
CPC ........ *C07K 14/43563* (2013.01); *A61P 31/10* (2018.01); *A61P 35/00* (2018.01); *C07K 5/08* (2013.01); *C07K 5/10* (2013.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS

| | | |
|---|---|---|
| 5,595,756 A | 1/1997 | Bally et al. |
| 6,004,925 A | 12/1999 | Dasseux et al. |
| 2011/0111424 A1 | 5/2011 | Rush, II et al. |
| 2011/0166321 A1 | 7/2011 | Garibay et al. |

FOREIGN PATENT DOCUMENTS

| | | |
|---|---|---|
| JP | 2016-526020 A | 9/2016 |
| WO | 2010/037395 A2 | 4/2010 |
| WO | 2014/182172 A1 | 11/2014 |
| WO | 2017/096247 A1 | 6/2017 |

OTHER PUBLICATIONS

International Search Report mailed Apr. 24, 2018, issued in corresponding International Application No. PCT/FR2018/050072, filed Jan. 12, 2018, 4 pages.
Written Opinion of the International Searching Authority mailed Apr. 24, 2018, issued in corresponding International Application No. PCT/FR2018/050072, filed Jan. 12, 2018, 10 pages.
Hara, M., et al.,"The role of hydrophobic amino acids of K-segments in the cryoprotection of lactate dehydrogenase by dehydrins," Journal of Plant Physiology; Dec. 14, 2016; pp. 18-23; vol. 210.

(Continued)

*Primary Examiner* — Thomas S Heard
(74) *Attorney, Agent, or Firm* — Christensen O'Connor Johnson Kindness PLLC

(57) ABSTRACT

The present invention relates to an isolated peptide consisting of a sequence of 3 to 39 amino acids derived from the amino acid sequence SEQ ID NO: 1, said peptide having a sequence of amino acids selected from the group consisting of:
a) sequences of 3 to 39 amino acids comprising at least the residues 6 to 8 of SEQ ID NO: 1, and
b) sequences of 3 to 39 amino acids having at least 70% identity with said sequence in a).

6 Claims, 10 Drawing Sheets
Specification includes a Sequence Listing.

(56) References Cited

OTHER PUBLICATIONS

Bravo, R.V., et al., "Amino terminal peptides of the ring infected erythrocyte surface antigen of Plasmodium falciparum bind specifically to erythrocytes," Vaccine; Jan. 1, 2000; pp. 1289-1293; vol. 18; No. 14.

Rifflet, A., et al., "Identification and characterization of a novel antimicrobial peptide from the venom of the ant Tetramorium bicarinatum," Peptides; Dec. 1, 2012; pp. 363-370; vol. 38; No. 2.

Aili, S.R., et al., "Diversity of peptide toxins from stinging ant venoms," Toxicon; Dec. 1, 2014; pp. 166-178; vol. 92.

Touchard, A., et al., "The Biochemical Toxin Arsenal from Ant Venoms," Toxins; Jan. 20, 2016; 28 pages total; vol. 8, No. 1.

Téné, N., et al., "Biochemical and biophysical combined study of bicarinalin, an ant venom antimicrobial peptide"; Peptides; Apr. 4, 2016; pp. 103-113; vol. 79.

Cendrowicz et al.; "The Role of Macrophages in Cancer Development and Therapy" Cancers (Basel); 2021; vol. 13; Issue No. 8.

Zhao, R. et al.; "Molecular Cloning of Two Novel Temporins From Lithobates catesbeianus and Studying of Their Antimicrobial Mechanisms"; Progress in Biochem. and Biophysics; May 2009; pp. 1064-1070; vol. 36; No. 8.

Conlon, J.M. et al. "Comparative peptidomics of the endocrine pancreas: islet hormones from the clawed frog Xenopus laevis and the red-bellied newt Cynops pyrrhogaster," Journal of Endocrinology; Dec. 2002; pp. 769-777; vol. 175.

Li et al.; "Cerebrin prohormone processing, distribution and action in Aplysia californica," Journ. of Neurochem.; Jun. 2001; pp. 1569-1580; vol. 277.

Yao, S. et al.; "Selective amplification by auto- and cross-catalysis in a replicating peptide system"; Nature; Dec. 1998; pp. 447-450; vol. 396.

Johnsen, A.H. et al. "Unique progaslrin processing in equine G-ceHs suggests marginal tyrosyl sulfotransferase ~ctivity"; Eur. J. Biochem.; Jul. 1998; pp. 432-438; vol. 255; No. 2.

Office Action issued in corresponding Japanese Application No. 2019-538129 mailed Oct. 12, 2021, 17 pages.

Examination report issued in corresponding Australian Application No. 2018207318 mailed Nov. 1, 2021, 8 pages.

FIG. 13B  FIG. 13C  FIG. 13D  FIG. 13E

IMMUNOMODULATORY PEPTIDE

CROSS REFERENCE TO RELATED PATENT APPLICATIONS

This patent application is continuation of U.S. patent application Ser. No. 16/476,788, filed Jul. 9, 2019, which is a National Stage of International Application No. PCT/FR2018/050072, filed Jan. 12, 2018, which claims the benefit of French Patent Application No. 1750280, filed Jan. 12, 2017, the entire disclosures of which are hereby incorporated by reference in their entirety for all purposes.

REFERENCE TO SEQUENCE LISTING

The Sequence Listing associated with this application is provided in XML format and is hereby incorporated by reference into the specification. The name of the XML file containing the sequence listing is 2023 12 15—PAT2519898US00—Sequence listing.xml. The XML file is 77.4 KB, was created on Dec. 15, 2023; and is being submitted via Patent Center with the filing of the specification.

FIELD OF THE INVENTION

The present invention relates to an isolated peptide, a pharmaceutical composition comprising this peptide and the use of this peptide or this composition as medication, in particular as an anti-infective or anticancer medicament.

TECHNOLOGICAL BACKGROUND

With the increasing emergence of resistant pathogens and the rarefaction of anti-infectives capable of fighting against these infections, the need to develop new therapeutic strategies has never been as urgent.

One of these strategies aims to activate the immune system with the development of immunomodulatory agents, capable in particular of strengthening the action of the immune system against pathogens.

SUMMARY OF THE INVENTION

The inventors have discovered that the peptide P17 and the derivatives thereof would have an immunomodulatory activity.

The peptide P17 is a peptide present in the venom of *Tetramorium bicarinatum* ants. This peptide of 13 amino acids had been described by Rifflet et al. (Identification and characterization of a novel antimicrobial peptide from the venom of the ant *Tetramorium bicarinatum*. Peptides. 2012 December; 38(2):363-70) but had thus shown no useful property. In particular, it had shown no in vitro antibacterial property.

The inventors have shown that, surprisingly, P17 and the derivatives thereof increased the release of pro-inflammatory cytokines and favoured the secretion of oxygen free radicals. The immunomodulation generated by P17 and the derivatives thereof is such that it makes it possible to eliminate pathogens like the yeast *C. albicans* and to decrease the proliferation of cancer cells by derivative macrophages of human monocytes thus polarised.

This immunomodulation is mediated by type C lectin receptors like the mannose or dectin-1 receptor which intervene in the innate immune response against numerous pathogens. These receptors recognise molecular patterns, such as glucans, present on the surface of numerous pathogens and expressed abnormally on the surface of cancer cells, P17 and derivatives thereof are therefore particularly promising candidates for the treatment or the prevention of numerous pathologies such as fungal, bacterial, viral or cancer pathologies.

Consequently, the present invention relates to an isolated peptide consisting of a sequence of 3 to 39 amino acids derived from the amino acid sequence SEQ ID NO: 1, said peptide having a sequence of amino acids selected from the group consisting of:
  a) sequences of 3 to 39 amino acids comprising at least the residues 6 to 8 of SEQ ID NO: 1, and
  b) sequences of 3 to 39 amino acids having at least 70% identity with said sequence in a),
  excluding the peptide having the amino acid sequence SEQ ID NO: 1.

The present invention also relates to a pharmaceutical composition comprising:
  a peptide according to the invention
  and
  a pharmaceutically acceptable excipient.

The present invention also relates to an isolated peptide intended to be used as a medicament; the isolated peptide consisting of a sequence of 3 to 39 amino acids derived from the amino acid sequence SEQ ID NO: 1 characterised in that said peptide has a sequence of amino acids selected from the group consisting of:
  a) sequences of 3 to 39 amino acids comprising at least the residues 6 to 8 of SEQ ID NO: 1, and
  b) sequences of 3 to 39 amino acids having at least 70% identity with said sequence in a).

DETAILED DESCRIPTION OF THE INVENTION

Peptides

The present invention relates to an isolated peptide consisting of a sequence of 3 to 39 amino acids derived from the amino acid sequence SEQ ID NO: 1 characterised in that said peptide has a sequence of amino acids selected from the group consisting of:
  a) sequences of 3 to 39 amino acids comprising at least the residues 6 to 8 of SEQ ID NO: 1, and
  b) sequences of 3 to 39 amino acids having at least 70%, 80%, 90% or 95% identity with said sequence in a),
  excluding the peptide having the amino acid sequence SEQ ID NO: 1.

The percentage of identity of a sequence of amino acids is defined by the percentage of amino acid residues in a sequence to be compared, which are identical to a reference sequence after alignment of sequences, by introducing spaces if necessary, so as to obtain a maximum sequence identity. The percentage of identity is then determined according to the following formula: Percentage of identity=$100 \times [1-(C/R)]$, such that C is the number of differences between the reference sequence and the sequence to be compared over the whole length of the reference sequence, (i) each amino acid in the reference sequence which has no corresponding amino acid aligned in the sequence to be compared, (ii) each space in the reference sequence and (iii) each amino acid aligned in the reference sequence which is different from an amino acid in the sequence to be compared, constitutes a difference, and R is the number of amino acids in the reference sequence over the whole length of the alignment with the sequence to be compared (i.e. the whole length of the reference sequence), each space generated in the reference sequence being counted as an amino acid. The alignment of sequences in view of determining the percentage of identity of a sequence can be produced in different manner known to a person skilled in the art, for example, by using public software available, like BLAST (Altschul et al, J. Mol. Biol., 1990, 215, 403-). This software is preferably used with the default parameters.

According to an embodiment, said isolated peptide consists of a sequence of 3 to 39 amino acids derived from the amino acid sequence SEQ ID NO: 1 and has a sequence of amino acids selected from the group consisting of:
 a) sequences of 3 to 39 amino acids comprising at least the residues 5 to 8 of SEQ ID NO: 1, and
 b) sequences of 3 to 39 amino acids having at least 70%, 80%, 90% or 95% identity with said sequence in a), excluding the peptide having the amino acid sequence SEQ ID NO: 1.

The peptides according to the invention can have 3 to 30, 3 to 26, or more preferably, 5 to 20 amino acids or even more preferably, 5 to 15 amino acids. For example, the isolated peptide can have 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids.

Advantageously, said peptide has a sequence of amino acids selected from the group consisting of:
 a) sequences of 3 to 39 amino acids comprising at least the residues 5 to 9 of SEQ ID NO: 1, and
 b) sequences of 3 to 39 amino acids having at least 70% identity with said sequence in a), excluding the peptide having the amino acid sequence SEQ ID NO: 1.

Preferably, the peptides according to the invention comprise at least the residues 1, 2, 3, 4, 5 or 6 to 8, 9, 10, 11, 12 or 13 of SEQ ID NO: 1 or have sequences of amino acids having at least 70%, 80%, 90% or 95% identity with said peptides comprising at least the residues 1, 2, 3, 4, 5 or 6 to 8, 9, 10, 11, 12 or 13 of SEQ ID NO: 1.

More specifically, the peptides according to the invention comprise at least the residues 1, 2, 3, 4, 5 or 6 to 8, 9, 10, 11, 12 or 13 of SEQ ID NO: 1.

The positions of the amino acid residues are indicated in reference to the sequence of P17 (SEQ ID NO: 1).

According to an embodiment, the peptides have at least 95% identity with said sequence defined above.

Preferably, the peptide is capable of being bound to the macrophage membrane derived from monocytes. It can trigger signalling pathways responsible for the production of cytotoxic mediators.

Preferably, the peptide is capable of inducing the production of oxygen free radicals and of IL-1β by macrophages derived from monocytes. The capacity of peptides to induce the production of oxygen free radicals and of IL-1β can easily be measured by a person skilled in the art. Such tests are, in particular, described in the section, Materials and Methods described below.

Advantageously, the peptide consists of a sequence of 5 to 15 amino acids comprising at least the residues 5 to 9 of the amino acid sequence SEQ ID NO: 1.

According to an embodiment, the peptide consists of a sequence of amino acids selected from the group consisting of:
 α) SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, and
 β) sequences of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids having at least 70%, 80%, 90%, 95% identity with said sequence a),
excluding the peptide having the amino acid sequence SEQ ID NO: 1.

More preferably, the peptide consists of a sequence of amino acids selected from the group consisting of:
 α) SEQ ID NO: 2, SEQ ID NO: 3, SEQ ID NO: 4, SEQ ID NO: 5, SEQ ID NO: 13, SEQ ID NO: 14, SEQ ID NO: 15, SEQ ID NO: 16 and SEQ ID NO: 17, and
 β) sequences of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids having at least 70%, 80%, 90%, 95% identity with said sequence a), excluding the peptide having the amino acid sequence SEQ ID NO: 1.

The different sequences are summarised in table 1 below:

TABLE 1

Sequences of amino acids

| Name | SEQ ID NO | Sequence of amino acids |
|---|---|---|
| P17 | 1 | LFKEILEKIKAKL |
| P17(2-13) | 2 | FKEILEKIKAKL |
| P17(3-13) | 3 | KEILEKIKAKL |
| P17(4-13) | 4 | EILEKIKAKL |
| P17(5-13) | 5 | ILEKIKAKL |
| P17(6-13) | 6 | LEKIKAKL |
| P17(7-13) | 7 | EKIKAKL |
| P17(8-13) | 8 | KIKAKL |
| P17(9-13) | 9 | IKAKL |
| P17(1-5) | 10 | LFKEI |
| P17(1-6) | 11 | LFKEIL |
| P17(1-7) | 12 | LFKEILE |
| P17(1-8) | 13 | LFKEILEK |
| P17(1-9) | 14 | LFKEILEKI |
| P17(1-10) | 15 | LFKEILEKIK |
| P17(1-11) | 16 | LFKEILEKIKA |
| P17(1-12) | 17 | LFKEILEKIKAK |

Advantageously, the peptides are recombinant or synthetic peptides. Thus, the peptides can be prepared by conventional techniques known to a person skilled in the art, in particular by solid or liquid phase synthesis or by expression of a recombinant DNA in a suitable cell system (eukaryote or prokaryote). For example, the peptides can be synthesised in solid phase, originally described by Merrifield et al (J. Am. Chem. Soc, 1964, 85: 2149-2154) according to the Fmoc technique and purified by inverted phase high-performance liquid chromatography. Preferably, the peptides are synthetic peptides.

Generally, the invention comprises peptides according to the invention having been subjected to a modification as long as said peptide conserves the immunomodulatory properties thereof.

The invention, in particular, comprises natural variant or synthetic peptides, obtained by mutation (insertion, deletion, substitution) of one or more amino acids in the sequence of P17 (SEQ ID NO: 1) as long as said peptide derived from P17 conserves the immunomodulatory properties thereof.

The peptides can be amidated at the C-terminal. The peptides can be acylated at the N-terminal. Preferably, the peptides are amidated at the C-erminal. By "amidated at the C-terminal", this conventionally means the presence of an $NH_2$ group at the C-terminal end of the peptide (non-substituted primary amide).

The invention also relates to the peptides modified at the C-terminal having a modification other than the amidation at the C-terminal described below, as long as said peptide derived from modified P17 conserves the immunomodulatory properties thereof. Also, the non-substituted primary amide ($RCONH_2$) at the C-terminal of the peptide amidated at the C-terminal can, for example, be replaced by a mono-substituted primary amide ($RCONHR_1$) ora disubstituted primary amide ($RCONR_1R_2$).

According to an embodiment, the peptide having the amino acid sequence SEQ ID NO: 1 and being amidated at the C-terminal is excluded.

In particular, the invention comprises the peptides derived from P17 or of a peptide such as defined above wherein certain amino acids have been substituted by an amino acid with similar properties. For example, hydrophobic amino acids such as the residues L1, L6 and L13, F2, I5, I9 and/or A11 can be substituted by another hydrophobic amino acid selected from the group consisting of A, V, L, I, M, F, W and non-natural hydrophobic amino acids such as tert leucine; the residues K3, K8, K10 and/or K12 can be substituted by another natural basic amino acid such as R and/or H or non-natural, such as ornithine, homolysine and/or para-aminophenylalanine; the residues E4 and/or E7 can be substituted by another amino acid such as D or a non-natural amino acid such as para-carboxyphenylalanine.

The peptide can, for example, consist of a variant of P17 or of a derivative of P17, such as described above, wherein one or more hydrophobic amino acids such as the residues L1, L6 and L13, F2, I5, I9 and/or A11 have been replaced by another hydrophobic amino acid selected from the group consisting of A, V, L, I, M, F, W and non-natural hydrophobic amino acids such as tert leucine.

Preferably, the residues K8, K10 and/or K12 are conserved. More preferably, the residues K3, K8, K10 and/or K12 are conserved.

According to an embodiment, the isolated peptide consists of a sequence of 5 to 20 amino acids derived from the amino acid sequence SEQ ID NO: 1;
said peptide has an amino acid sequence selected from the group consisting of:
a) sequences of 5 to 20 amino acids comprising at least the residues 6 to 8 of SEQ ID NO: 1, and
b) sequences of 5 to 20 amino acids having at least 70%, 80%, 90% or 95% identity with said sequence in a), excluding the peptide having the amino acid sequence SEQ ID NO: 1
and said peptide is amidated at the C-terminal.

According to an embodiment, the isolated peptide consists of a sequence of 5 to 20 amino acids derived from the amino acid sequence SEQ ID NO: 1; said peptide has a sequence of amino acids selected from the group consisting of:
a) sequences of 5 to 20 amino acids comprising at least the residues 5 to 8 of SEQ ID NO: 1, and
b) sequences of 5 to 20 amino acids having at least 70%, 80%, 90% or 95% identity with said sequence in a), excluding the peptide having amino acid sequence SEQ ID NO: 1
and said peptide is amidated at the C-terminal.

According to an embodiment, the isolated peptide consists of a sequence of 5 to 20 amino acids derived from the amino acid sequence SEQ ID NO: 1; said isolated peptide has a sequence of amino acids selected from the group consisting of:
α) SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16 and SEQ ID NO: 17, and
β) sequences of 5 to 20 amino acids having at least 70%, 80%, 90% or 95% identity with said sequence a)
and said peptide is amidated at the C-terminal.

According to an embodiment, the isolated peptide consists of a sequence of 5 to 20 amino acids derived from the amino acid sequence SEQ ID NO: 1; said isolated peptide has a sequence of amino acids selected from the group constituted of:
α) SEQ ID NO: 2, SEQ ID NO: 3, SEQ ID NO: 4, SEQ ID NO: 5, SEQ ID NO: 6, SEQ ID NO: 16 and SEQ ID NO: 17, and
β) sequences of 5 to 20 amino acids having at least 70%, 80%, 90% or 95% identity with said sequence a)
and said peptide is amidated in C-terminal.

The present invention also relates to a multimer of peptides according to the invention and/or the peptide having the amino acid sequence SEQ ID NO: 1, said peptides being amidated at the C-terminal or not. For example, the invention can relate to a dimer or a trimer. The multimer can be a homomer or a heteromer.

Polynucleotides

The present invention also relates to an isolated polynucleotide encoding a peptide such as defined above ora peptide P17.

According to the invention, the sequence of said polynucleotide is that of the cDNA encoding said peptide. Said sequence can advantageously be modified such that the use of codons is optimal in the host wherein it is expressed.

The present invention also relates to a recombinant vector comprising said polynucleotide.

Preferably, said vector is an expression vector comprising all the elements necessary for the expression of the peptide. For example, said vector comprises an expression cassette including at least one polynucleotide such as defined above, under the regulatory control of the suitable transcription and possibly the translation (promotor, activator, intron, initiation codon (ATG), codon stop, polyadenylation signal, splicing site).

The present invention also relates to a modified prokaryote or eukaryote host, comprising a peptide, a polynucleotide or a vector such as defined above; the cell could be stably or transiently modified.

Pharmaceutical Composition

The present invention also relates to a pharmaceutical composition characterised in that it comprises a peptide such as defined above and a pharmaceutically acceptable excipient.

The composition can also comprise the peptide P17 and a pharmaceutically acceptable excipient.

According to an alternative embodiment, the pharmaceutical composition can comprise
   a peptide consisting of a sequence of 3 to 39 amino acids derived from the amino acid sequence SEQ ID NO: 1 characterised in that said peptide has a sequence of amino acids selected from the group consisting of:
   a) sequences of 3 to 39 amino acids comprising at least the residues 6 to 8 of SEQ ID NO: 1, and
   b) sequences of 3 to 39 amino acids having at least 70% identity with said sequence in a),
   and
   a pharmaceutically acceptable excipient.

According to an alternative embodiment, the pharmaceutical composition can comprise
   a peptide consisting of a sequence of 3 to 39 amino acids derived from the amino acid sequence SEQ ID NO: 1 characterised in that said peptide has a sequence of amino acids selected from the group consisting of:
   a) sequences of 3 to 39 amino acids comprising at least the residues 5 to 8 of SEQ ID NO: 1, and
   b) sequences of 3 to 39 amino acids having at least 70% identity with said sequence in a),
   and
   a pharmaceutically acceptable excipient.

The peptides of the pharmaceutical composition can have 3 to 30, 3 to 26, or more preferably, 5 to 20 amino acids or even more preferably, 5 to 15 amino acids. For example, the isolated peptide can have 3, 4, 5, 6, 7, 8, 9, 10, 11, 12, 13, 14, 15, 16, 17, 18, 19, 20, 21, 22, 23, 24, 20 25, 26, 27, 28, 29, 30, 31, 32, 33, 34, 35, 36, 37, 38 or 39 amino acids.

The composition can, in particular, comprise a peptide consisting of a sequence of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids derived from the amino acid sequence SEQ ID NO: 1 characterised in that said peptide has a sequence of amino acids selected from the group consisting of:
   a) sequences of amino acids comprising at least the residues 1, 2, 3, 4, 5 or 6 to 8, 9, 10, 11, 12 or 13 of SEQ ID NO: 1, and
   b) sequences of amino acids having at least 70%, 80%, 90% or 95% identity with said sequence in a).

Advantageously, the composition can, in particular, comprise a peptide consisting of a sequence of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids derived from the amino acid sequence SEQ ID NO: 1 characterised in that said peptide has a sequence of amino acids selected from the group consisting of:
   a) sequences of amino acids comprising at least the residues 1, 2, 3, 4 or 5 to 9, 10, 11, 12 or 13 of SEQ ID NO: 1, and
   b) sequences of amino acids having at least 70%, 80%, 90% or 95% identity with said sequence in a).

According to an embodiment, the pharmaceutical composition comprises a peptide having a sequence of amino acids selected from the group consisting of:
   α) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, and
   β) sequences of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids having at least 70%, 80%, 90%, 95% identity with said sequence a).

According to a preferred embodiment, the pharmaceutical composition comprises a peptide having a sequence of amino acids selected from the group consisting of:
   α) SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16 and SEQ ID NO: 17, and
   β) sequences of 3 to 39 amino acids having at least 70%, 80%, 90% or 95% identity with said sequence a).

According to an embodiment, the peptide having the amino acid sequence SEQ ID NO: 1 is excluded from the pharmaceutical composition. According to an embodiment, the peptide having the amino acid sequence SEQ ID NO: 1 and being amidated at the C-terminal is excluded from the pharmaceutical composition.

According to a variant, said peptide has the amino acid sequence SEQ ID NO: 1. According to an embodiment of this variant, the peptide has the amino acid sequence SEQ ID NO: 1 and is amidated at the C-terminal.

The peptides can be recombinant or synthetic peptides.

Generally, the invention comprises peptides according to the invention having been subjected to a modification, as long as said peptide conserves the immunomodulatory properties thereof.

The invention comprises, in particular, natural variant or synthetic peptides obtained by mutation (insertion, deletion, substitution) of one or more amino acids in the sequence of P17 (SEQ ID NO: 1) as long as said peptide derived from P17 conserves the immunomodulatory properties thereof.

The peptides can be amidated at the C-terminal. The peptides can be acylated at the N-terminal. Preferably, the peptides are amidated at the C-terminal. By "amidated at the C-terminal", this conventionally means the presence of an $NH_2$ group at the C-terminal end of the peptide (non-substituted primary amide).

The invention also relates to peptides modified at the C-terminal having a modification other than the amidation at the C-terminal described above, as long as said modified peptide derived from P17 conserves the immunomodulatory properties thereof. Also, the non-substituted primary amide ($RCONH_2$) at the C-terminal of the amidated peptide can, for example, be replaced by a monosubstituted primary amide ($RCONHR_1$) or a disubstituted amide ($RCONR_1R_2$).

The peptides can be natural or synthetic variants obtained by mutation of the abovementioned peptides. As indicated above, the variants can comprise a substitution of hydrophobic amino acids such as the residues L1, L6 and L13, F2, I5, I9 and/or A11 by another hydrophobic amino acid selected from the group consisting of A, V, L, I, M, F, W and non-natural hydrophobic amino acids, such as tert leucine, a substitution of the residues K3, K8, K10 and/or K12 by another natural basic amino acid such as R and/or H or non-natural such as ornithine, homolysine and/or para-aminophenylalanine and/or a substitution of the residues E4 and/or E7 by another acid amino acid such as D or a non-natural amino acid such as para-carboxyphenylalanine.

The peptide can, for example, consist of a variant of P17 or of a derivative of P17 such as described above, wherein one or more hydrophobic amino acids such as the residues L1, L6 and L13, F2, I5, I9 and/or A11 have been replaced by another hydrophobic amino acid selected from the group consisting of A, V, L, I, M, F, W and non-natural hydrophobic amino acids such as tert leucine.

Preferably, the residues K8, K10 and/or K12 are conserved. More specifically, the residues K3, K8, K10 and/or K12 are conserved.

The present invention also relates to a multimer of peptides according to the invention and/or the peptide having the amino acid sequence SEQ ID NO: 1, said peptides being amidated at the C-terminal or not. For example, the invention can relate to a dimer or a trimer. The multimer can be a homomer or a heteromer.

The pharmaceutically acceptable excipient can, for example, be a support selected from the group constituted of sterile water, a saline solution, glucose, dextrose or buffered solutions. The pharmaceutically acceptable excipient can also be a diluent, a stabiliser, a preservative, a wetting agent, an emulsifying agent, a buffer, an additive improving the viscosity. The PBS can be excluded from the pharmaceutically acceptable excipients.

The pharmaceutical composition comprises an effective dose of peptide making it possible to obtain a prophylactic/therapeutic effect. This dose is determined and adjusted according to factors such as age, sex and weight of the subject. The pharmaceutical composition is generally administered according to the usual protocols, to the doses, and for a sufficient duration to induce an immunomodulator effect. The administration can be subcutaneous, intramuscular, intravenous, intradermic, intraperitoneal, oral, sublingual, rectal, vaginal, intranasal, by inhalation or by transdermal application.

The pharmaceutical composition is presented in a galenic form, suitable for a selected administration: sterile, injectable solution, powder, tablets, capsules, suspension, syrup, suppositories, which are prepared according to standard protocols.

The pharmaceutical composition can further comprise another therapeutic agent. The therapeutic agent can be, for example, selected from the group consisting of an antifungal, an anticancer, an antiviral, an antiparasitic and an antibiotic.

Therapy

The inventors have shown that P17 and the derivatives thereof activated the cytotoxic functions of the macrophages derived from human peripheral blood monocytes. Thus, the macrophages polarised by P17 or the derivatives thereof have a high recognition and phagocytic capacity of pathogens, which express on the wall thereof of the conserved molecular structure (PAMP), and of the tumour cells, having altered glycan patterns, recognised by C-type lectin receptors.

The C-type lectin receptors are involved in the innate immune response against numerous pathogens, such as:
bacteria (Sukhithasri V. et al., Innate immune recognition of microbial cell wall components and microbial strategies to evade such recognitions, Microbiol Res. 2013 Aug. 25; 168(7):396-406, Killick K E et al., Receptor-mediated recognition of mycobacterial pathogens, Cell Microbiol. 2013 Sep; 15(9)),
fungi and yeasts (Vautier S et al., C-type lectin receptors and cytokines in fungal immunity, Cytokine. 2012 April; 58(1):89-99; Drummond R A et al., The role of Dectin-1 in the host defence against fungal infections, Curr Opin Microbiol. 2011 August; 14(4):392-9),
parasites (Vàzquez-Mendoza A. et al., Parasitic infections: a role for C-type lectins receptors, Biomed Res Int. 2013; 2013:456352 Epub 2013 25 Jan. 27, Lefèvre L. et al., The C-type lectin receptors dectin-1, MR, and SIGNR3 contribute both positively and negatively to the macrophage response to *Leishmania infantum*. Immunity. 2013 May 23; 38(5):1038-49)
as well as against tumour cells (Dube D H. Et al., Glycans in cancer and inflammation-potential for therapeutics and diagnostics, Nat Rev Drug Discov. 2005 June; 4(6):477-88, Aarnoudse C A et al., Recognition of tumor glycans by antigen-presenting cells, Curr Opin Immunol. 2006 February; 18(1):105-11, Chiba S et al. Recognition of tumor cells by Dectin-1 orchestrates innate immune cells for anti-tumor responses, Elife. 2014 Aug. 22; 3).

Consequently, the invention also relates to a peptide and/or a pharmaceutical composition comprising said peptide and a pharmaceutically acceptable excipient, intended to be used as medication, said peptide consisting of a sequence of 3 to 39 amino acids derived from the amino acid sequence SEQ ID NO: 1 characterised in that said peptide has a sequence of amino acids selected from the group consisting of:
a) sequences of 3 to 39 amino acids comprising at least the residues 6 to 8 of SEQ ID NO: 1, and
b) sequences of 3 to 39 amino acids having at least 70% identity with said sequence in a), The invention relates to a treatment method in a subject to be treated comprising the administration to said subject of an effective quantity of said peptide or of said pharmaceutical composition comprising said isolated peptide and a pharmaceutically acceptable excipient.

The invention also relates to the use of said peptide or of said pharmaceutical composition comprising said peptide and a pharmaceutically acceptable excipient in the production of a medication.

According to an embodiment, said peptide intended to be used as medication consists of a sequence of 3 to 39 amino acids derived from the amino acid sequence SEQ ID NO: 1, said peptide having a sequence of amino acids selected from the group consisting of:
a) sequences of 3 to 39 amino acids comprising at least the residues 5 to 8 of SEQ ID NO: 1, and
b) sequences of 3 to 39 amino acids having at least 70% identity with said sequence in a), Said peptide can have 3 to 30, 3 to 26, or more preferably, 5 to 20 amino acids, or even more preferably, 5 to 15 amino acids. For example, the isolated peptide can have 3, 4, 5, 6, 7, 8, 9, 10, 11, 12, 13, 14, 15, 16, 17, 18, 19, 20, 21, 22, 23, 24, 30 25, 26, 27, 28, 29, 30, 31, 32, 33, 34, 35, 36, 37, 38 or 39 amino acids.

Advantageously, said peptide can consist of a sequence of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids derived from the amino acid sequence SEQ ID NO: 1, said peptide having a sequence of amino acids selected from the group consisting of:
a) sequences of 3 to 39 amino acids comprising at least the residues 1, 2, 3, 4, 5 or 6 to 8, 9, 10, 11, 12 or 13 of SEQ ID NO: 1, and
b) sequences of 3 to 39 amino acids having at least 70%, 80%, 90% or 95% identity with said sequence in a).

Advantageously, said peptide consists of a sequence of 3, 4, 5, 6, 7, 8, 9, 10, 11, 12, 13, 14, 15, 16, 17, 18, 19, 20, 21, 22, 23, 24, 25, 10 26, 27, 28, 29, 30, 31, 32, 33, 34, 35, 36, 37, 38 or 39 amino acids derived from the amino acid sequence SEQ ID NO: 1 characterised in that said peptide has a sequence of amino acids selected from the group consisting of:

a) sequences of amino acids comprising at least the residues 1, 2, 3, 4 or 5 to 9, 10, 11, 12 or 13 of SEQ ID NO: 1, and
b) sequences of amino acids having at least 70%, 80%, 90% or 95% identity with said sequence in a).

According to an embodiment, the peptide has a sequence of amino acids selected from the group consisting of:
α) SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16 and SEQ ID NO: 17, and
β) sequences of 3, 4, 5, 6, 7, 8, 9, 10, 11, 12, 13, 14, 15, 16, 17, 18, 19, 20, 21, 22, 23, 24, 25, 25 26, 27, 28, 29, 30, 31, 32, 33, 34, 35, 36, 37, 38 or 39 amino acids having at least 70%, 80%, 90%, 95% identity with said sequence a).

According to a preferred embodiment, said peptide intended to be used as medication has a sequence of amino acids selected from the group consisting of:
α) SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16 and SEQ ID NO: 17, and
β) sequences of 3 to 39 amino acids having at least 70%, 80%, 90% or 95% identity with said sequence a).

According to a preferred embodiment, said peptide has the amino acid sequence SEQ ID NO: 1. According to a preferred embodiment, the peptide has the sequence if amino acids SEQ ID NO: 1 and is amidated in C-terminal.

According to an alternative embodiment, the peptide does not have the amino acid sequence SEQ ID NO: 1. According to an alternative embodiment, the peptide is not the peptide which has the amino acid sequence SEQ ID NO: 1 and which is amidated in C-terminal.

The peptides can be recombinant or synthesis peptides.

Generally, the invention comprises peptides according to the invention having been subjected to a modification, as long as said peptide conserves the immunomodulatory properties thereof.

The invention comprises, in particular, variant natural or synthetic peptides obtained by mutation (insertion, deletion, substitution) of one or more amino acids in the sequence of P17 (SEQ ID NO: 1) as long as said peptide derived from P17 conserves the immunomodulatory properties thereof.

The peptides can be amidated in C-terminal. The peptides can be acylated in N-terminal. Preferably, the peptides are amidated in C-terminal. By "amidated in C-terminal", this conventionally means the presence of an $NH_2$ group at the C-terminal end of the peptide (non-substituted primary amide).

The invention also relates to peptides modified at the C-terminal having a modification other than the amidation at the C-terminal described above, as long as said modified peptide derived from P17 conserves the immunomodulatory properties thereof. Also, the non-substituted primary amide ($RCONH_2$) at the C-terminal of the amidated peptide can, for example, be replaced by a monosubstituted primary amide ($RCONHR_1$) or a disubstituted amide ($RCONR_1R_2$).

The peptides can be natural or synthetic variants obtained by mutation of the abovementioned peptides. As indicated above, the variants can comprise a substitution of hydrophobic amino acids, such as the residues L1, L6 and L13, F2, I5, I9 and/or A11 by another hydrophobic amino acid selected from the group consisting of A, V, L, I, M, F, W and non-natural hydrophobic amino acids such as tert leucine, a substitution of the residues K3, K8, K10 and/or K12 by another natural basic amino acid R and/or H, or non-natural, such as ornithine, homolysine and/or para-aminophenylalanine and/or a substitution of the residues E4 and/or E7 by another acid amino acid such as D or a non-natural amino acid such as para-carboxyphenylalanine.

The peptide can, for example, consist of a variant of P17 or a derivative of P17 such as described above, wherein one or more hydrophobic amino acids such as the residues L1, L6 and L13, F2, I5, I9 and/or A11 have been replaced by another hydrophobic amino acid selected from the group consisting of A, V, L, I, M, F, W and non-natural hydrophobic amino acids such as tert leucine.

Preferably, the residues K8, K10 and/or K12 are conserved. More specifically, the residues K3, K8, K10 and/or K12 are conserved.

According to an embodiment, the isolated peptide consists of a sequence of 5 to 20 amino acids derived from the amino acid sequence SEQ ID NO: 1; said peptide has a sequence of amino acids selected from the group consisting of:
a) sequences of 5 to 20 amino acids comprising at least the residues 6 to 8 of SEQ ID NO: 1, and
b) sequences of 5 to 20 amino acids having at least 70%, 80%, 90% or 95% identity with said sequence in a),
and said peptide is amidated at the C-terminal.

More preferably, the isolated peptide consists of a sequence of 5 to 20 amino acids derived from the amino acid sequence SEQ ID NO: 1; said peptide has a sequence of amino acids selected from the group consisting of:
a) sequences of 5 to 20 amino acids comprising at least the residues 5 to 8 of SEQ ID NO: 1, and
b) sequences of 5 to 20 amino acids having at least 70%, 80%, 90% or 95% identity with said sequence in a),
and said peptide is amidated in C-terminal.

According to an embodiment, the isolated peptide consists of a sequence of 5 to 20 amino acids derived from the amino acid sequence SEQ ID NO: 1; said isolated peptide has a sequence of amino acids selected from the group consisting of:
α) SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16 and SEQ ID NO: 17, and
β) sequences of 5 to 20 amino acids having at least 70%, 80%, 90% or 95% identity with said sequence a)
and said peptide is amidated at the C-terminal.

According to an embodiment, the isolated peptide consists of a sequence of 5 to 20 amino acids derived from the amino acid sequence SEQ ID NO: 1; said isolated peptide has a sequence of amino acids selected from the group constituted of:
α) SEQ ID NO: 1, SEQ ID NO: 2, SEQ ID NO: 3, SEQ ID NO: 4, SEQ ID NO: 5, SEQ ID NO: 6, SEQ ID NO: 16 and SEQ ID NO: 17, and
β) sequences of 5 to 20 amino acids having at least 70%, 80%, 90% or 95% identity with said sequence a)
and said peptide is amidated at the C-terminal.

The present invention also relates to a multimer of peptides according to the invention and/or of the peptide having the amino acid sequence SEQ ID NO: 1, said peptides being amidated at the C-terminal or not. For example, the invention can relate to a dimer or a trimer. The multimer can be a homomer or a heteromer.

The inventors have shown that P17 and derivatives thereof would lead to the production of pro-inflammatory cytokines. Consequently, the invention also relates to said peptide or said pharmaceutical composition for the use thereof, as a pro-inflammatory agent.

The inventors have shown that the macrophages polarised by P17 would have an overexpression of C-type lectin receptors. These receptors are involved in the immune response against numerous pathogens.

Consequently, the invention relates to said peptide and/or said pharmaceutical composition by the use thereof in the prevention or the treatment of a disease caused by a pathogen recognised by C-type lectin receptors, preferably by mannose or dectin-1 receptors. Pathogens can be:
- a bacteria; for example, a bacteria selected from the group consisting of *Streptococcus pneumoniae, Klebellia pneumoniae, Cryptococcus neoformans* and *Mycobacterium tuberculis*,
- a fungus; for example *Candida albicans*,
- parasite; for example, a parasite selected from the group consisting of *Leishmania donovani, Pneumocystis carinii* and *Trypanosoma cruzi*.

The invention therefore relates to a method for preventing or treating a disease caused by a pathogen recognised by a C-type lectin receptor in a subject to be treated comprising the administration in said subject, of an effective quantity of said peptide or of said pharmaceutical composition comprising said isolated peptide and a pharmaceutically acceptable excipient.

The disease caused by a pathogen recognised by a C-type lectin receptor is preferably mycosis, more preferably, candidiasis.

C-type lectin receptors are also involved in the immune response against tumour cells. Consequently, said peptide can be for a use like an anti-cancer use; in the treatment of cancer.

The invention therefore also relates to a method for preventing or treating a cancer in a subject to be treated comprising the administration in said subject of an effective quantity of said peptide or of said pharmaceutical composition comprising said isolated peptide and a pharmaceutically acceptable excipient.

The invention will be furthermore illustrated by the following figures and examples. However, these examples and figures must not be interpreted as limiting the scope of the present invention.

FIGURES

FIGS. 13A-13E show the effect of administering P17 in mice infected over the capacity of the peritoneal macrophages thereof (FIGS. 13A-13B) to remove and phagocytose *Candida albicans*, (FIG. 13C) to produce ROS, and (FIGS. 13D-13E) to release IL-β and IL-12.

EXAMPLES

Equipment and Methods

P17 Anti-Microbial Peptide

Figure 1:
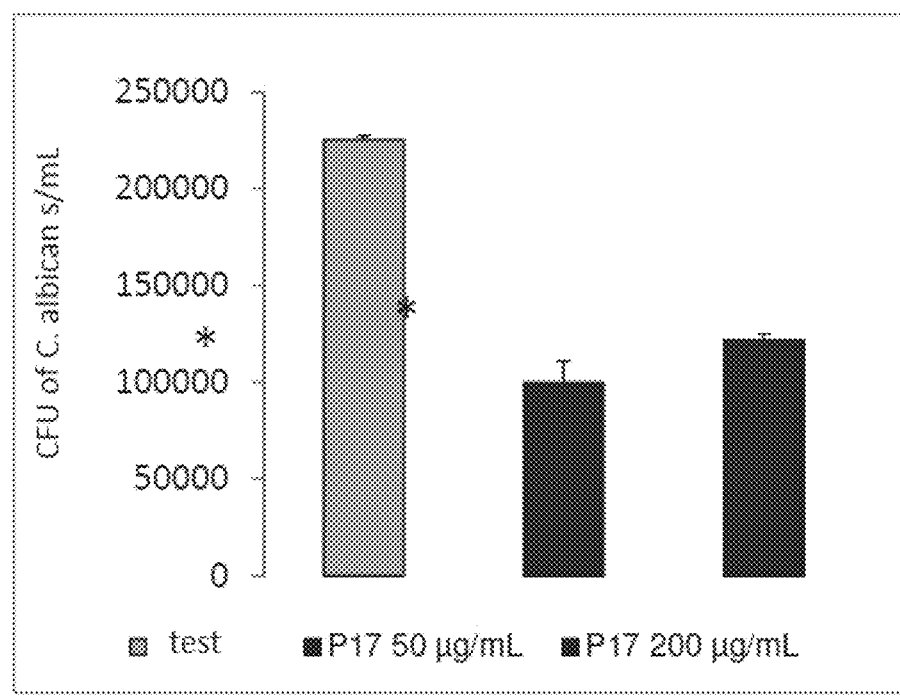
FIG. 1 shows the removal of *C. albicans* by macrophages derived from human monocytes treated, or untreated, by the in vitro P17.

Unless it is specified otherwise, the peptide P17 used in the figures and the examples below is amidated at the C-terminal (presence of an $NH_2$ group at the C-terminal end thereof). The sequence thereof has been characterised by de novo sequencing by using mass spectrometry and Edman degradation (Rifflet et al. 2012). The peptide P17 has been synthesised on an automated Liberty peptide synthesiser (CEM, Saclay, France) with a purity greater than 99%. The molecular authenticity and identity of synthetic peptides have been tested by MALDI-TOF-MS.

Study of Removing *C. albicans* by Macrophages Derived from Human Monocytes

The macrophages derived from human monocytes have been treated, or not, with the peptide P17 or fragments of it then incubated at 37° C. for 24 hours. These cells have been incubated for 40 minutes at 37° C. with C. albicans (at a ratio of 0.3 yeasts per macrophage) and the non-bound yeasts are removed by washing. These macrophages are thus incubated at 37° C. for 4 hours. After incubation, the environment has been removed and the cells have been lysed. The units forming colonies (CFU) of *C. albicans* have been determined on Sabouraud boxes after spreading and culturing for 48 hours at 37° C.

Study of Binding and of the Phagocytosis of *C. albicans* by Macrophages Derived from Human Monocytes To analyse the binding and the phagocytosis of *C. albicans*, macrophages derived from human monocytes have been treated, or not, with the peptide P17, then incubated at 37° C. for 24 hours. The macrophages derived from human monocytes have been brought together with the yeasts marked GFP (ratio 1/6) then incubated at 4° C. for 20 minutes, in order to evaluate the binding. The phagocytosis has been evaluated after 1 hour of incubation at 37° C. The quantity of *C. albicans* bound or ingested by macrophages derived from human monocytes has been determined by measuring the fluorescence by using a fluorimeter (PerkinElmer EnVision).

Study of the Production of ROS by Macrophages Derived from Human Monocytes in Response to *C. albicans*

To analyse the production of ROS, the macrophages derived from human monocytes have been treated, or not, with the peptide P17, P17, non-amidated, or with the following P17 fragments, P17(1-5), P17(1-7), P17(1-9), P17(1-11), P17(3-13), P17(5-13), P17(7-13) and P17(9-13); the fragments P17(1-5), P17(1-7), P17(1-9), P17(1-11) not being amidated at the C-terminal 20 and the fragments P17(3-13), P17(5-13), P17(7-13) and P17(9-13) being amidated at the C-terminal. Then, the macrophages derived from human monocytes thus treated have been incubated at 37° C. for 24 hours. The production of reactive derivatives of oxygen (ROS) has been measured by chemiluminescence in the presence of 5-amino-2,3-dihydro-1,4-phthalazinedione (luminol) (EnVision; PerkinElmer). The chemiluminescence generation has been continually measured for 1 hour 30 minutes after incubation of cells with luminol (66 µM) in the presence, or not, of *C. albicans* (yeast ratio per macrophage: 3:1).

Study of Production of ROS by Murine Macrophages in Response to Murine Lymphoma T Tumour Cells (EL4)

To analyse the production of ROS, peritoneal murine macrophages have been treated, or not, with the peptide P17 then incubated at 37° C. for 24 hours. The production of reactive derivatives of oxygen (ROS) has been measured by chemiluminescence in the presence of 5-amino-2,3-dihydro-1,4-phthalazinedione (luminol) (EnVision; PerkinElmer). The chemiluminescence generation has been continually measured for 1 hour 30 minutes after incubation of cells with luminol (66pM) in the presence, or not, of EL4 lymphoma T tumour cells.

Study of the Production of IL-1β, TNFα, IL-10 and IL-12 by Macrophages Derived from Human Monocytes in Response to *C. albicans*

Macrophages derived from human derivatives have been stimulated with the peptide P17 for 24 hours, then these macrophages activated by the peptide P17 have been stimulated with *C. albicans* at a yeast per macrophage ratio of 3:1 for 8 hours. The production of IL-1β, TNFα, IL-10 and IL-12 in cell supernatants has been determined by ELISA (OptiElA BD Biosciences).

Evaluation of the Protein Expression of C-Type Lectin Receptors

To analyse the protein level of C-type lectin receptors, the macrophages derived from human monocytes have been treated, or not, with the peptide P17 (200 µg/ml) then incubated at 37° C. for 24 hours. The cells collected have been centrifugated at 1500 rpm for 10 minutes and nerve cells have been suspended in the PBS supplemented with 1% foetal calf serum (FCS). The cells have been marked with antibodies coupled with different fluorochromes directed against the Dectin-1 receptor (mAb; R&D FAB1859C-100, 1/40), DC-SIGN (mAb; BD Biosciences 551 265, 1/20) CD16 (mAb; PNIM 0814, 1/20), CD36 (mAb; BD Biosciences 550 956, 1/40) and the mannose receptor (specific MR (mannose receptor) ligand) conjugated FITC (Sigma A7790, 1 mg/ml 1/100)). The analysis has been carried out by flow cytometry (Becton Dickinson FACScalibur) over a population of 10000 cells.

Reverse Transcription and PCR in Real Time

Macrophages derived from human monocytes have been treated with P17 (200 µg/ml) for 8 hours. The preparation of DNA has been carried out by using a kit (EZ-10 Spin Column Total RNA Minipreps Super Kit by Bio Basic) and by following the instructions of the manufacturer. The synthesis of cDNA has been carried out according to the instructions of the manufacturer (Thermo Electron). An RT-qPCR has been produced on a LightCycler 480 system by using the LightCycler SYBR Green I Master (Roche Diagnostics). Primers (Eurogentec) have been produced with the software Primer 3. The mRNA of GAPDH has been used as a control. Pooled cDNA samples diluted in series have been used as external standard in each series for the quantification.

The sequences of primers are given in the table below.

TABLE

| Gene | | Sequence 5'-3' | |
|---|---|---|---|
| Alox5 | antisense | ACT-GGA-AAC-ACG-GCA-AAA-AC | (SEQ ID NO: 18) |
| | sense | TTT-CTC-AAA-GTC-GGC-GAA-GT | (SEQ ID NO: 19) |
| Itgam (CD11b) | antisense | TTG-CAT-CCA-TCT-CAA-ATC-CA | (SEQ ID NO: 20) |
| | sense | CTC-CCA-AAG-TGC-TGG-GAT-TA | (SEQ ID NO: 21) |
| Fcgr3 (CD16) | antisense | TAC-AGC-GTG-CTT-GAG-AAG-GA | (SEQ ID NO: 22) |
| | sense | GCA-CCT-GTA-CTC-TCC-ACT-GT | (SEQ ID NO: 23) |

Sequences of human primers used in qPCR analysis

TABLE-continued

Sequences of human primers used in qPCR analysis

| Gene | | Sequence 5'-3' |
|---|---|---|
| Fcgr2 (CD32) | antisense sense | CCA-AAG-GCT-GTG-CTG-AAA-CT (SEQ ID NO: 24)<br>TAC-TCC-CCG-CTG-TCA-TTG-TT (SEQ ID NO: 25) |
| Cd36 | antisense sense | TGA-TAG-GTG-CAG-CAA-AGC-AC (SEQ ID NO: 26)<br>TGT-AAC-CCA-GGA-CGC-TGA-GG (SEQ ID NO: 27) |
| Clec7a (Dectin-1) | antisense sense | CCA-AGC-ATA-GGA-TTC-CCA-AAA (SEQ ID NO: 28)<br>AAA-AGG-ATC-GTG-TGC-TGC-ATC (SEQ ID NO: 29) |
| Ptgs2 (COX-2) | antisense sense | TGA-GCA-TCT-ACG-GTT-TGC-TG (SEQ ID NO: 30)<br>TGC-TTG-TCT-GGA-ACA-ACT-GC (SEQ ID NO: 31) |
| Pla2g4a (cPLA2) | antisense sense | GCC-TTG-GTG-AGT-GAT-TCA-GCT (SEQ ID NO: 32)<br>AGA-TTC-AAG-CCC-AGC-ATG-AAG (SEQ ID NO: 33) |
| Cd209 (DC-SIGN) | antisense sense | GGG-CAT-GGA-GGC-TCC-AC (SEQ ID NO: 34)<br>CAA-CTT-AGA-AAC-AGC-CAA-ATG-GAA (SEQ ID NO: 35) |
| Alox5ap (FLAP) | antisense sense | ACC-CGC-TCA-AAG-GCA-ATG-G (SEQ ID NO: 36)<br>CAC-GAA-AGC-AGG-ACC-CAG-A (SEQ ID NO: 37) |
| Gapdh | antisense sense | AGG-TCG-GAG-TCA-ACG-GAT-TT (SEQ ID NO: 38)<br>ATC-TCG-CTC-CTG-GAA-GAT-GG (SEQ ID NO: 39) |
| Il1b | antisense sense | CAG-CCA-ATC-TTC-ATT-GCT-CA (SEQ ID NO: 40)<br>AGG-CAG-AGA-GGG-AAG-GAG-AG (SEQ ID NO: 41) |
| Il6 | antisense sense | TAC-CCC-CAG-GAG-AAG-ATT-GT (SEQ ID NO: 42)<br>TTT-TCT-GCC-AGT-GCC-TCT-TT (SEQ ID NO: 43) |
| Il12 | antisense sense | TGG-GTG-GGT-CAG-GTT-TGA-TG (SEQ ID NO: 44)<br>GCC-CAG-CTG-CTG-AGG-AGA-GT (SEQ ID NO: 45) |
| Il10 | antisense sense | TGC-AAA-ACC-AAA-CCA-CAA-GA (SEQ ID NO: 46)<br>TCT-CGG-AGA-TCT-CGA-AGC-AT (SEQ ID NO: 47) |
| Il1ra | antisense sense | TGG-GAA-TCT-CAG-ATG-GGA-AG (SEQ ID NO: 48)<br>CTG-TGT-CCC-CCA-GAA-CTT-GT (SEQ ID NO: 49) |
| Tgfb1 | antisense sense | ACT-GAG-GGG-AAG-GGA-CAA-CT (SEQ ID NO: 50)<br>TCG-GTA-CCA-GGT-GAG-GGT-AG (SEQ ID NO: 51) |
| p47$^{phox}$ | antisense sense | CCT-CAT-TGT-CCA-GTG-TGG-TG (SEQ ID NO: 52)<br>TCT-TCC-GTC-TCG-TCA-GGA-CT (SEQ ID NO: 53) |
| Lta4h | antisense sense | ACT-GCT-TGG-AGG-ACC-AGA-GA (SEQ ID NO: 54)<br>GGA-AAG-CAT-TAG-CAG-GCA-AG (SEQ ID NO: 55) |
| Mrc-1 (MR) | antisense sense | GGC-GGT-GAC-CTC-ACA-AGT-AT (SEQ ID NO: 56)<br>ACG-AAG-CCA-TTT-GGT-AAA-CG (SEQ ID NO: 57) |
| Ptges (PGES) | antisense sense | CAT-GTG-AGT-CCC-TGT-GAT-GG (SEQ ID NO: 58)<br>GAC-TGC-AGC-AAA-GAC-ATC-CA (SEQ ID NO: 59) |
| Pparg | antisense sense | GCT-GTG-CAG-GAG-ATC-ACA-GA (SEQ ID NO: 60)<br>GGG-CTC-CAT-AAA-GTC-ACC-AA (SEQ ID NO: 61) |
| Tnfα | antisense sense | TCC-TTC-AGA-CAC-CCT-CAA-CC (SEQ ID NO: 62)<br>AGG-CCC-CAG-TTT-GAA-TTC-TT (SEQ ID NO: 63) |

Determination of the Intracellular Calcium Concentration

The intracellular calcium concentration has been measured by using a Fluo 3-AM fluorescent probe (Molecular Probe). Macrophages derived from human monocytes ($1.5 \times 10^5$) have been incubated with $11.5 \times 10^{-6}$ M of Fluo 3-AM for 30 minutes at 37° C. The intracytosolic Ca2+l evel has been recorded every 0.5 seconds for a total period of 3 minutes after the addition of P17 (200 µg/ml). In desensitisation experiments, a second injection of N-Formylmethionine-leucyl-phenylalanine (fMLP) bacterial peptide of P17 has been carried out at the end of the recording of the fluorescence and the level of intracytosolic Ca2+ level recorded for 3 minutes in addition. In certain experiments, macrophages derived from human monocytes have been preincubated with U73122 (2 µM) or HBSS without calcium for 10 minutes before the addition of P17. The fluorescence has been quantified by using the approach based on EnVision fluorimetry (PerkinElmer).

Experimental Gastrointestinal Candida Murine Model

For in vivo experiments, a gastrointestinal infection with the *C. albicans* strain 98/26135 has been established by feeding with $50 \times 10^6$ of *C. albicans* per mouse (n=8 per group). No antibiotic or immunosuppressant treatment has been used to facilitate the infection of mucous membranes of the oral cavity and of the gastrointestinal tract. The mice have been treated intraperitoneally (i.p.) with the peptide P17 (10 μg per mouse) or with a saline solution for control groups, 1 day before the injection with *C. albicans*, 1 day after infection and then every 2 days (5 injections). The body weight of each mouse has been recorded daily. On the $8^{th}$ day after treatment (7 days after infection), all mice have been euthanised by asphyxiation with $CO_2$.

The oesophagus, the stomach, the caecum and the liver have been removed aseptically to evaluate the colonisation by *C. albicans*. The peritoneal macrophages of the mice have been sampled and the ex vivo capacities thereof to remove and to phagocytose *Candida albicans* have been determined. The production of ROS, IL-(3 and IL-12 by these macrophages in response to *Candida albicans* have also been evaluated.

Quantification of the Number of Lymphoma T Tumour Cells (EL4) in the Presence of Murine Macrophages Peritoneal murine macrophages have been treated, or not, with the peptide P17 then incubated at 37° C. for 24 hours. These macrophages have been incubated for 40 minutes at 37° C. with luminescent lymphoma T cells (EL4-luc) and unbound cells are removed by washing. These macrophages are thus incubated at 37° C. for 4 hours. After incubation, the number of lymphoma T cells (EL4-luc) is evaluated by chemiluminescence.

Results

FIG. 1 shows that the presence of P17 considerably increases the capacity of human macrophages to remove in vitro *C. albicans*.

Figure 11:
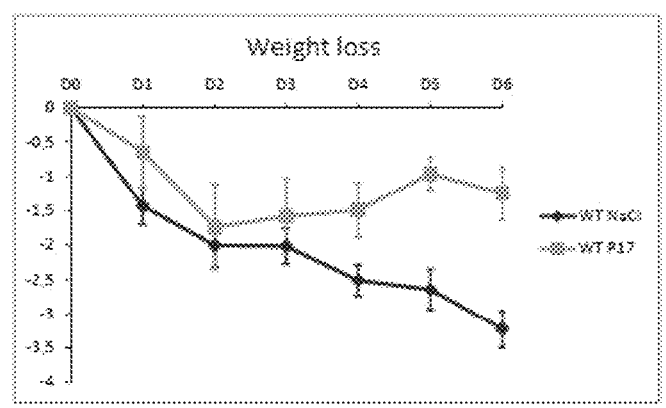
FIG. 11 shows the effects of administering in vitro P17 on the body weight of mice having a gastrointestinal candidiasis induced by *C. albicans*.
Figure 12:
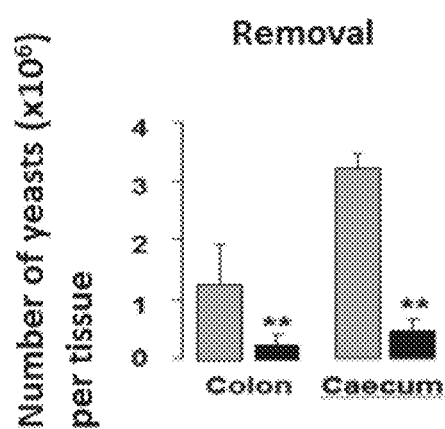
FIG. 12 shows the effect of administering in vivo P17 on the gastrointestinal colonisation, 6 days post-infection.
Figure 13A:
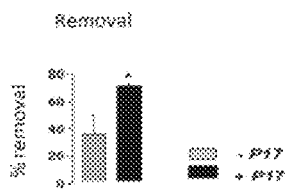
Figure 14:
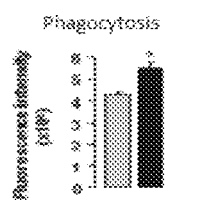
FIG. 14 illustrates the mode of action of P17.
Figure 14:
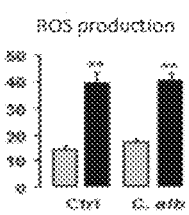
Figure 14:
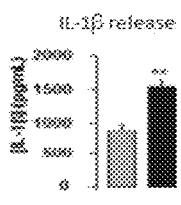
Figure 14:
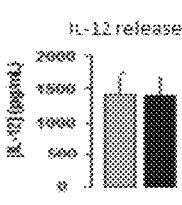
Figure 14:
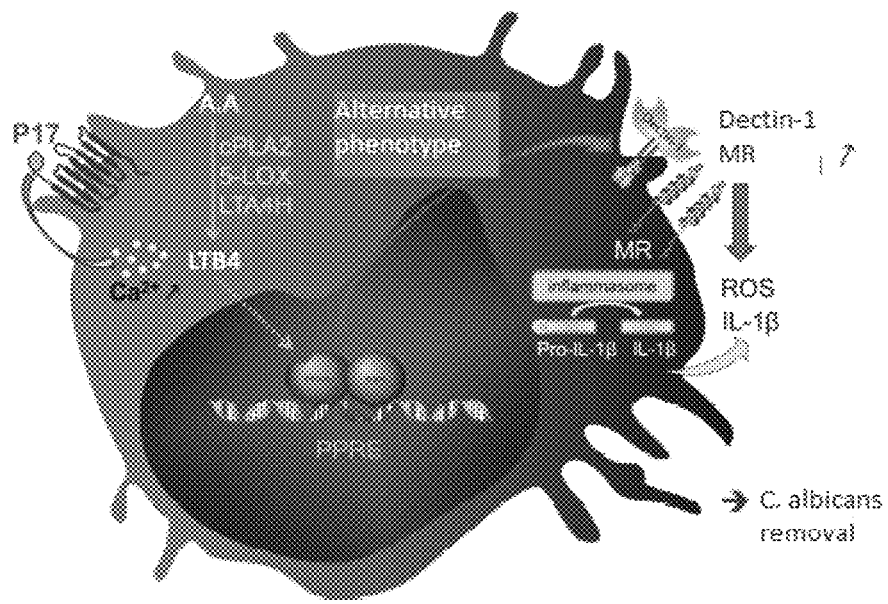

These results have been confirmed in vivo on mice infected by *C. albicans*. Indeed, mice having a gastrointestinal candidiasis treated by P17 would have a lesser loss of weight with respect to untreated mice (FIG. 11). Consistently, the gastrointestinal colonisation by *Candida albicans* was significantly lower in mice treated by P17 with respect to untreated mice (FIG. 12).

The inventors have sought to understand the mechanism underlying the action of P17.

Figure 2:
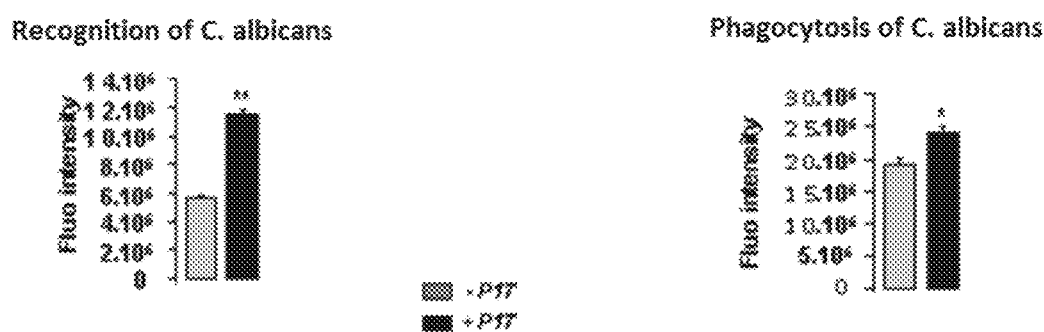
FIG. 2 shows the binding and phagocytic capacity of *C. albicans* by macrophages derived from human monocytes treated or untreated by the P17.
Figure 3:
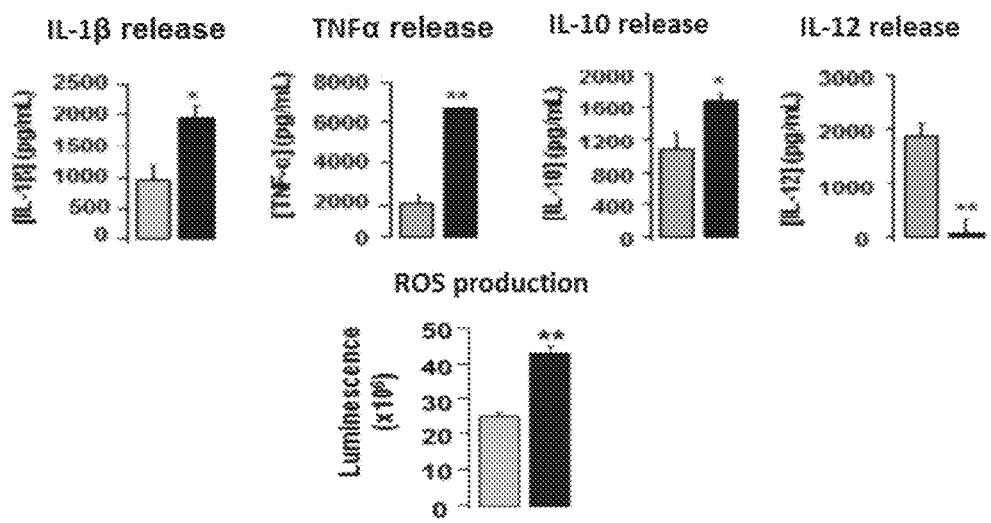
FIG. 3 shows the effect of P17 on the production of oxygen free radicals (OFR) and cytokines, such as 1L-1β, TNFα, IL-10 and IL-12, by macrophages derived from human monocytes in response to a stimulation by *C. albicans*.
Figure 4:
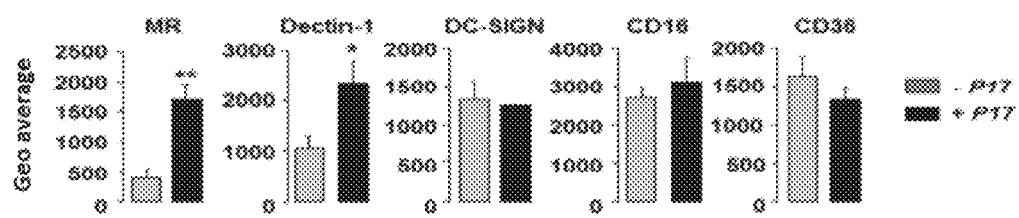
FIG. 4 shows the effect of P17 on the protein expression of C-type lectin receptors.
Figure 5:
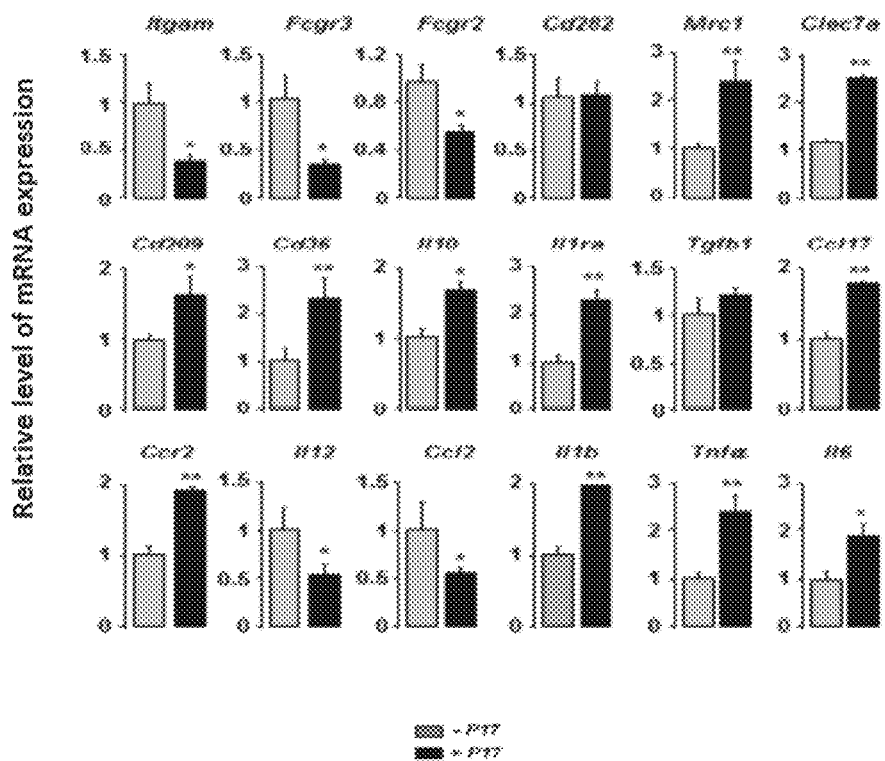
FIG. 5 shows the effect of P17 on the expression of marker genes of the conventional and alternative differentiation of the macrophages.
Figure 6:
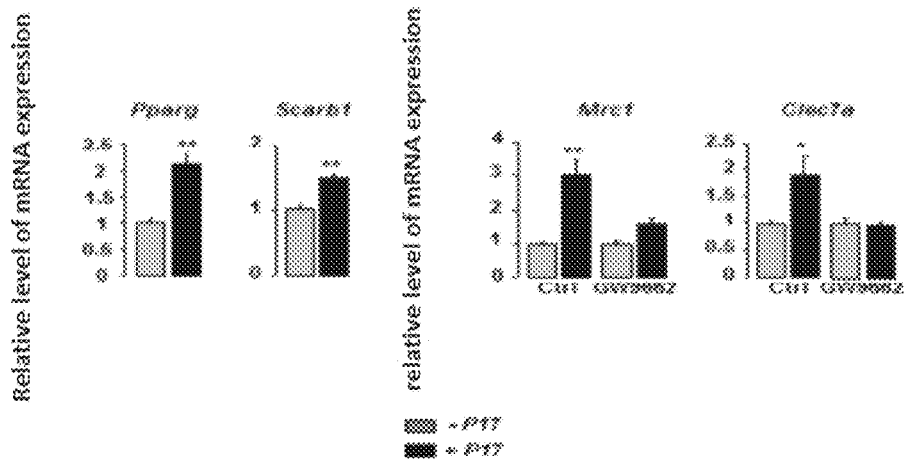
FIG. 6 shows the effect of P17 on the expression of encoding genes PPAR-γ and the target SRB1 thereof, and on the expression of membrane receptors Dectin-1 and MR in the presence of GW9662, an irreversible antagonist of PPAR-γ in macrophages derived from human monocytes.
Figure 7:
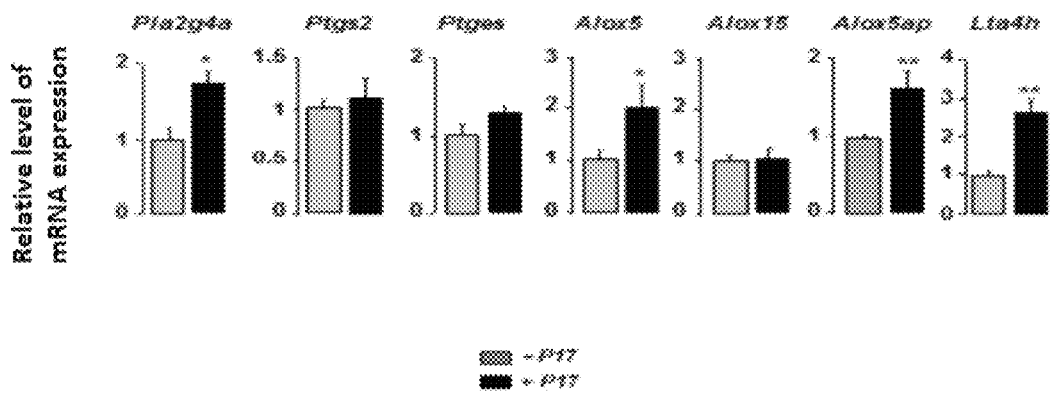
FIG. 7 shows the effect of P17 on the expression of genes encoding enzymes of the metabolism of arachidonic acid in macrophages derived from human monocytes.
Figure 8:
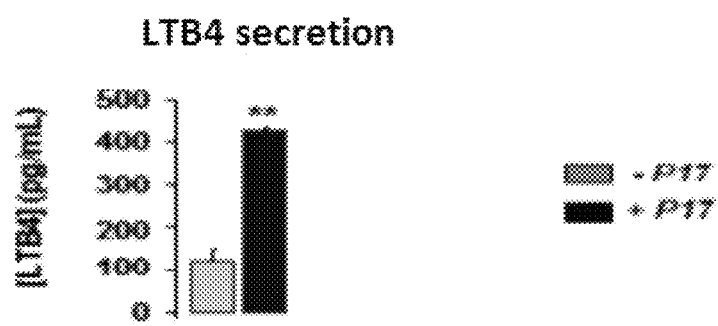
FIG. 8 shows the effect of P17 on the secretion of LTB4 by macrophages derived from human monocytes.
Figures 9A, 9B, 9C:
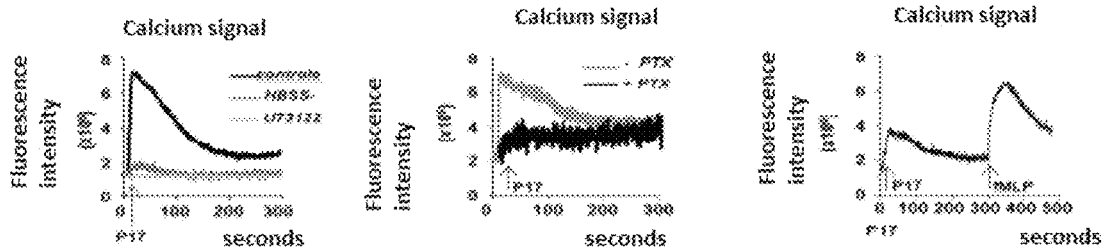
FIGS. 9A-9C represent the intracellular calcium concentration induced by P17 with respect to negative tests (FIG. 9A), in the presence of pertussis toxin (FIG. 9B) and by desensitising with fMLP (peptide N-Formylmethionine-leucyl-phenylalanine) (FIG. 9C).
Figure 10:
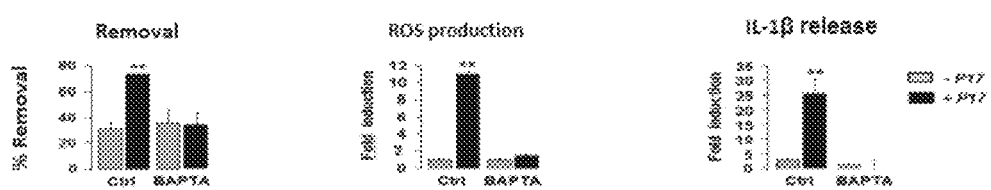
FIG. 10 shows the effect of BAPTA (calcium binder) on the antimicrobial effect of P17, the release of reactive derivatives of oxygen (ROS) and of IL-16.

The macrophages derived from human monocytes treated by P17 both have a greater capacity to recognise and to phagocytose *C. albicans* (FIGS. 2). In addition, P17 induces a higher production of ROS in response to stimulation by *C. albicans* and pro-inflammatory cytokines such as IL-1β and TNFα (FIG. 3). The increase of producing these cytotoxic mediators by the peptide P17 is associated with the overexpression of C-type lectin receptors on the surface of macrophages derived from human monocytes (FIG. 4).

P17 Improves the Anti-Tumour Response of the Macrophages

Figure 15:
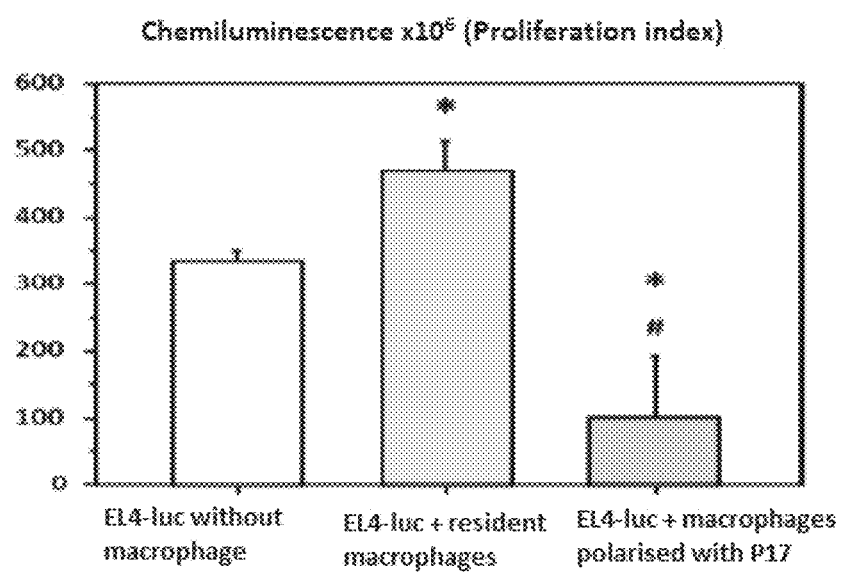
FIG. 15 shows the number of T lymphoma cells (EL4) in co-culture with macrophages treated or untreated by P17.

As FIG. 15 shows, in the presence of macrophages polarised by P17, the number of EL4 tumour cells decreases significantly. These results reveal that the macrophages polarised by P17 have a significant cytotoxic activity regarding tumour cells, with respect to untreated microphages.

Figure 16:
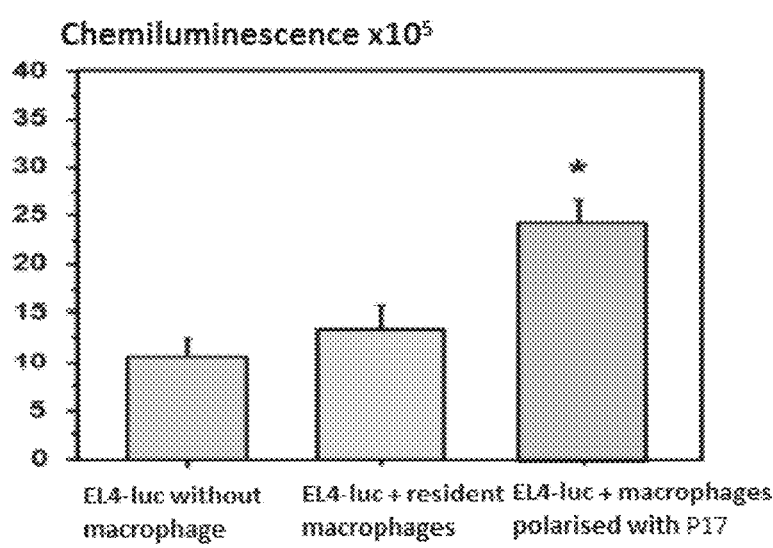
FIG. 16 shows the ROS production capacity of macrophages treated, or untreated, by P17 in response to EL4 tumour cells.

This induction of cytotoxic activity of the macrophages by P17 regarding tumour cells is correlated with an increased production of ROS (FIG. 16).

Effects of P17 Fragments on the Production of Reactive Species of Oxygen (ROS) and on the Removal of *Candida albicans* by Macrophages The capacity to induce the release of ROS in response to *C. albicans* of macrophages treated by different P17 fragments has been tested.

Figure 17:
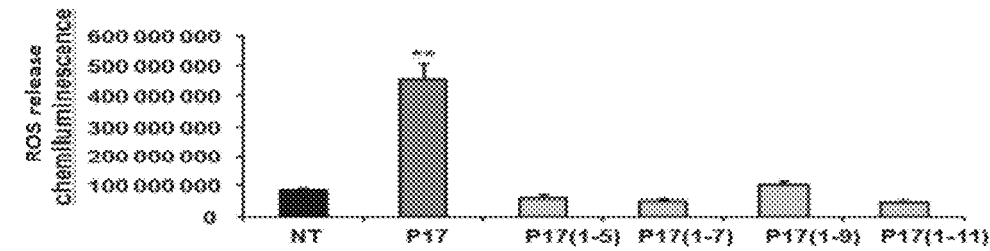
FIG. 17 shows the effect of different fragments of P17 on the release of ROS by macrophages derived from human monocytes in response to *C. albicans*.
Figure 17:
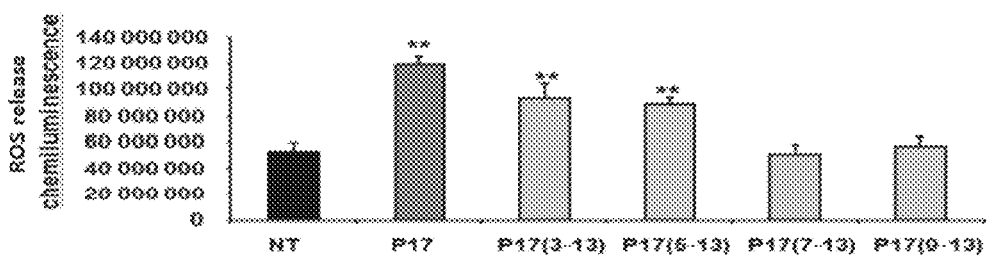
Figure 18:
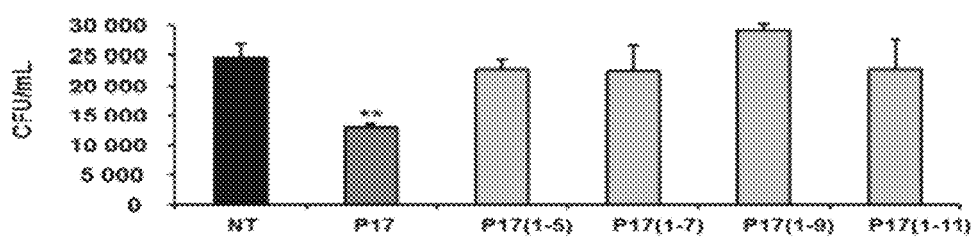
FIG. 18 shows the effect of different fragments of P17 on the removal of *Candida albicans* by macrophages derived from human monocytes.
Figure 18:
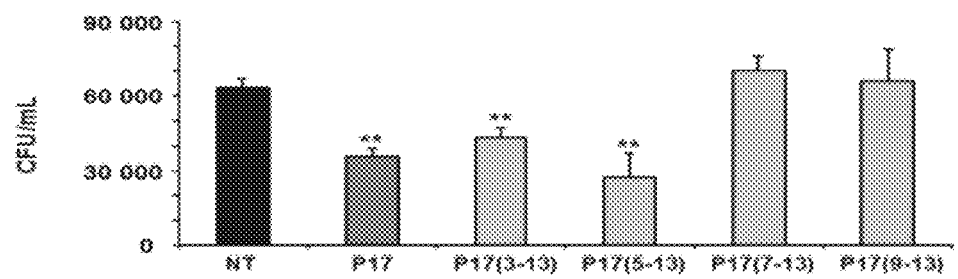

The results obtained with the peptides which lack the C-terminal end (P17(1-5), P17(1-7), P17(1-9), P17(1-11)) shows the importance of this region in the activation of the cytotoxic functions of the macrophages by P17 (FIGS. 17-18). Indeed, the treatment of macrophages with these fragments does not induce the production of ROS, nor the removal of *Candida albicans*.

Figure 19:
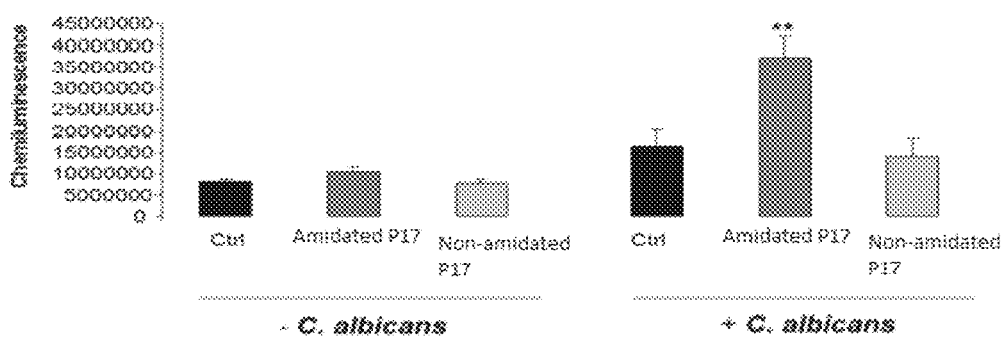
FIG. 19 shows the effect of C-terminal amidation of P17 on the production of ROS by macrophages in response to *C. albicans*.

The peptides P17(1-5), P17(1-7), P17(1-9), P17(1-11) tested were not amidated at the C-terminal contrary to P17. The difference of ROS release between amidated P17 and non-amidated P17 has therefore been tested in order to determine the impact of the C-terminal amidation on the pro-inflammatory properties of P17. These results show that the C-terminal amidation of P17 is essential to the pro-inflammatory activity thereof (FIG. 19).

The ROS release induced by the fragments from which the N-terminal portion has been deleted (P17(3-13), P17(5-13), P17(7-13), P17(9-13)) has also been tested. Only the fragments P17(3-13) and P17(5-13) conserve the activity thereof (FIG. 17). These results show the major role of central amino acids in the immunomodulatory activity of P17.

The effects of the different fragments on the removal of *C. albicans* by the macrophages have also been tested. The results are identical to those obtained for the release of ROS. Fragments with no C-terminal portion are inactive, while the fragments P17(3-13) and P17(5-13) have an activity close to that of P17.

---

The invention claimed is:

1. An isolated peptide consisting of a sequence of amino acids selected from the group consisting of SEQ ID NO:1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16, and SEQ ID NO: 17,
wherein the peptide is amidated at the C-terminal and
wherein the peptide is a pro-inflammatory agent that increases expression of C-type lectin receptors on the surface of macrophages.

2. The isolated peptide according to claim 1 wherein the peptide is capable of being bound to the membrane of macrophages derived from monocytes.

3. A pharmaceutical composition, comprising:
the peptide according to claim 1
and
a pharmaceutically acceptable excipient.

4. The isolated peptide according to claim 1, wherein the peptide has the amino acid sequence selected from the group consisting of SEQ ID NO:1, SEQ ID NO: 2, SEQ ID NO:

3, SEQ ID NO: 4, SEQ ID NO: 5 and SEQ ID NO: 6 and is amidated at the C-terminal.

5. The isolated peptide according to claim 1, wherein the peptide has the amino acid sequence SEQ ID NO: 1 and is amidated at the C-terminal.

6. The isolated peptide according to claim 1, wherein the peptide acylated at the N-terminal.

* * * * *

SEQUENCE LISTING

```
Sequence total quantity: 63
SEQ ID NO: 1          moltype = AA  length = 13
FEATURE               Location/Qualifiers
source                1..13
                      mol_type = protein
                      organism = Tetramorium bicarinatum
SEQUENCE: 1
LFKEILEKIK AKL                                                    13
```

-continued

```
SEQ ID NO: 2              moltype = AA  length = 12
FEATURE                   Location/Qualifiers
REGION                    1..12
                          note = Synthetic peptide
source                    1..12
                          mol_type = protein
                          organism = synthetic construct
SEQUENCE: 2
FKEILEKIKA KL                                                                12

SEQ ID NO: 3              moltype = AA  length = 11
FEATURE                   Location/Qualifiers
REGION                    1..11
                          note = Synthetic peptide
source                    1..11
                          mol_type = protein
                          organism = synthetic construct
SEQUENCE: 3
KEILEKIKAK L                                                                 11

SEQ ID NO: 4              moltype = AA  length = 10
FEATURE                   Location/Qualifiers
REGION                    1..10
                          note = Synthetic peptide
source                    1..10
                          mol_type = protein
                          organism = synthetic construct
SEQUENCE: 4
EILEKIKAKL                                                                   10

SEQ ID NO: 5              moltype = AA  length = 9
FEATURE                   Location/Qualifiers
REGION                    1..9
                          note = Synthetic peptide
source                    1..9
                          mol_type = protein
                          organism = synthetic construct
SEQUENCE: 5
ILEKIKAKL                                                                    9

SEQ ID NO: 6              moltype = AA  length = 8
FEATURE                   Location/Qualifiers
REGION                    1..8
                          note = Synthetic peptide
source                    1..8
                          mol_type = protein
                          organism = synthetic construct
SEQUENCE: 6
LEKIKAKL                                                                     8

SEQ ID NO: 7              moltype = AA  length = 7
FEATURE                   Location/Qualifiers
REGION                    1..7
                          note = Synthetic peptide
source                    1..7
                          mol_type = protein
                          organism = synthetic construct
SEQUENCE: 7
EKIKAKL                                                                      7

SEQ ID NO: 8              moltype = AA  length = 6
FEATURE                   Location/Qualifiers
REGION                    1..6
                          note = Synthetic peptide
source                    1..6
                          mol_type = protein
                          organism = synthetic construct
SEQUENCE: 8
KIKAKL                                                                       6

SEQ ID NO: 9              moltype = AA  length = 5
FEATURE                   Location/Qualifiers
REGION                    1..5
                          note = Synthetic peptide
source                    1..5
                          mol_type = protein
                          organism = synthetic construct
SEQUENCE: 9
IKAKL                                                                        5
```

```
SEQ ID NO: 10          moltype = AA   length = 5
FEATURE                Location/Qualifiers
REGION                 1..5
                       note = Synthetic peptide
source                 1..5
                       mol_type = protein
                       organism = synthetic construct
SEQUENCE: 10
LFKEI                                                                  5

SEQ ID NO: 11          moltype = AA   length = 6
FEATURE                Location/Qualifiers
REGION                 1..6
                       note = Synthetic peptide
source                 1..6
                       mol_type = protein
                       organism = synthetic construct
SEQUENCE: 11
LFKEIL                                                                 6

SEQ ID NO: 12          moltype = AA   length = 7
FEATURE                Location/Qualifiers
REGION                 1..7
                       note = Synthetic peptide
source                 1..7
                       mol_type = protein
                       organism = synthetic construct
SEQUENCE: 12
LFKEILE                                                                7

SEQ ID NO: 13          moltype = AA   length = 8
FEATURE                Location/Qualifiers
REGION                 1..8
                       note = Synthetic peptide
source                 1..8
                       mol_type = protein
                       organism = synthetic construct
SEQUENCE: 13
LFKEILEK                                                               8

SEQ ID NO: 14          moltype = AA   length = 9
FEATURE                Location/Qualifiers
REGION                 1..9
                       note = Synthetic peptide
source                 1..9
                       mol_type = protein
                       organism = synthetic construct
SEQUENCE: 14
LFKEILEKI                                                              9

SEQ ID NO: 15          moltype = AA   length = 10
FEATURE                Location/Qualifiers
REGION                 1..10
                       note = Synthetic peptide
source                 1..10
                       mol_type = protein
                       organism = synthetic construct
SEQUENCE: 15
LFKEILEKIK                                                            10

SEQ ID NO: 16          moltype = AA   length = 11
FEATURE                Location/Qualifiers
REGION                 1..11
                       note = Synthetic peptide
source                 1..11
                       mol_type = protein
                       organism = synthetic construct
SEQUENCE: 16
LFKEILEKIK A                                                          11

SEQ ID NO: 17          moltype = AA   length = 12
FEATURE                Location/Qualifiers
REGION                 1..12
                       note = Synthetic peptide
source                 1..12
                       mol_type = protein
                       organism = synthetic construct
SEQUENCE: 17
```

LFKEILEKIK AK                                                                              12

SEQ ID NO: 18          moltype = DNA   length = 20
FEATURE                Location/Qualifiers
misc_feature           1..20
                       note = Primer
source                 1..20
                       mol_type = other DNA
                       organism = synthetic construct
SEQUENCE: 18
actggaaaca cggcaaaaac                                                                      20

SEQ ID NO: 19          moltype = DNA   length = 20
FEATURE                Location/Qualifiers
misc_feature           1..20
                       note = Primer
source                 1..20
                       mol_type = other DNA
                       organism = synthetic construct
SEQUENCE: 19
tttctcaaag tcggcgaagt                                                                      20

SEQ ID NO: 20          moltype = DNA   length = 20
FEATURE                Location/Qualifiers
misc_feature           1..20
                       note = Primer
source                 1..20
                       mol_type = other DNA
                       organism = synthetic construct
SEQUENCE: 20
ttgcatccat ctcaaatcca                                                                      20

SEQ ID NO: 21          moltype = DNA   length = 20
FEATURE                Location/Qualifiers
misc_feature           1..20
                       note = Primer
source                 1..20
                       mol_type = other DNA
                       organism = synthetic construct
SEQUENCE: 21
ctcccaaagt gctgggatta                                                                      20

SEQ ID NO: 22          moltype = DNA   length = 20
FEATURE                Location/Qualifiers
misc_feature           1..20
                       note = Primer
source                 1..20
                       mol_type = other DNA
                       organism = synthetic construct
SEQUENCE: 22
tacagcgtgc ttgagaagga                                                                      20

SEQ ID NO: 23          moltype = DNA   length = 20
FEATURE                Location/Qualifiers
misc_feature           1..20
                       note = Primer
source                 1..20
                       mol_type = other DNA
                       organism = synthetic construct
SEQUENCE: 23
gcacctgtac tctccactgt                                                                      20

SEQ ID NO: 24          moltype = DNA   length = 20
FEATURE                Location/Qualifiers
misc_feature           1..20
                       note = Primer
source                 1..20
                       mol_type = other DNA
                       organism = synthetic construct
SEQUENCE: 24
ccaaaggctg tgctgaaact                                                                      20

SEQ ID NO: 25          moltype = DNA   length = 20
FEATURE                Location/Qualifiers
misc_feature           1..20
                       note = Primer
source                 1..20
                       mol_type = other DNA
                       organism = synthetic construct

```
SEQUENCE: 25
tactccccgc tgtcattgtt                                                    20

SEQ ID NO: 26            moltype = DNA   length = 20
FEATURE                  Location/Qualifiers
misc_feature             1..20
                         note = Primer
source                   1..20
                         mol_type = other DNA
                         organism = synthetic construct
SEQUENCE: 26
tgataggtgc agcaaagcac                                                    20

SEQ ID NO: 27            moltype = DNA   length = 20
FEATURE                  Location/Qualifiers
misc_feature             1..20
                         note = Primer
source                   1..20
                         mol_type = other DNA
                         organism = synthetic construct
SEQUENCE: 27
tgtaacccag gacgctgagg                                                    20

SEQ ID NO: 28            moltype = DNA   length = 21
FEATURE                  Location/Qualifiers
misc_feature             1..21
                         note = Primer
source                   1..21
                         mol_type = other DNA
                         organism = synthetic construct
SEQUENCE: 28
ccaagcatag gattcccaaa a                                                  21

SEQ ID NO: 29            moltype = DNA   length = 21
FEATURE                  Location/Qualifiers
misc_feature             1..21
                         note = Primer
source                   1..21
                         mol_type = other DNA
                         organism = synthetic construct
SEQUENCE: 29
aaaaggatcg tgtgctgcat c                                                  21

SEQ ID NO: 30            moltype = DNA   length = 20
FEATURE                  Location/Qualifiers
misc_feature             1..20
                         note = Primer
source                   1..20
                         mol_type = other DNA
                         organism = synthetic construct
SEQUENCE: 30
tgagcatcta cggtttgctg                                                    20

SEQ ID NO: 31            moltype = DNA   length = 20
FEATURE                  Location/Qualifiers
misc_feature             1..20
                         note = Primer
source                   1..20
                         mol_type = other DNA
                         organism = synthetic construct
SEQUENCE: 31
tgcttgtctg gaacaactgc                                                    20

SEQ ID NO: 32            moltype = DNA   length = 21
FEATURE                  Location/Qualifiers
misc_feature             1..21
                         note = Primer
source                   1..21
                         mol_type = other DNA
                         organism = synthetic construct
SEQUENCE: 32
gccttggtga gtgattcagc t                                                  21

SEQ ID NO: 33            moltype = DNA   length = 21
FEATURE                  Location/Qualifiers
misc_feature             1..21
                         note = Primer
source                   1..21
                         mol_type = other DNA
```

```
                          organism = synthetic construct
SEQUENCE: 33
agattcaagc ccagcatgaa g                                            21

SEQ ID NO: 34             moltype = DNA   length = 17
FEATURE                   Location/Qualifiers
misc_feature              1..17
                          note = Primer
source                    1..17
                          mol_type = other DNA
                          organism = synthetic construct
SEQUENCE: 34
gggcatggag gctccac                                                 17

SEQ ID NO: 35             moltype = DNA   length = 24
FEATURE                   Location/Qualifiers
misc_feature              1..24
                          note = Primer
source                    1..24
                          mol_type = other DNA
                          organism = synthetic construct
SEQUENCE: 35
caacttagaa acagccaaat ggaa                                         24

SEQ ID NO: 36             moltype = DNA   length = 19
FEATURE                   Location/Qualifiers
misc_feature              1..19
                          note = Primer
source                    1..19
                          mol_type = other DNA
                          organism = synthetic construct
SEQUENCE: 36
acccgctcaa aggcaatgg                                               19

SEQ ID NO: 37             moltype = DNA   length = 19
FEATURE                   Location/Qualifiers
misc_feature              1..19
                          note = Primer
source                    1..19
                          mol_type = other DNA
                          organism = synthetic construct
SEQUENCE: 37
cacgaaagca ggacccaga                                               19

SEQ ID NO: 38             moltype = DNA   length = 20
FEATURE                   Location/Qualifiers
misc_feature              1..20
                          note = Primer
source                    1..20
                          mol_type = other DNA
                          organism = synthetic construct
SEQUENCE: 38
aggtcggagt caacggattt                                              20

SEQ ID NO: 39             moltype = DNA   length = 20
FEATURE                   Location/Qualifiers
misc_feature              1..20
                          note = Primer
source                    1..20
                          mol_type = other DNA
                          organism = synthetic construct
SEQUENCE: 39
atctcgctcc tggaagatgg                                              20

SEQ ID NO: 40             moltype = DNA   length = 20
FEATURE                   Location/Qualifiers
misc_feature              1..20
                          note = Primer
source                    1..20
                          mol_type = other DNA
                          organism = synthetic construct
SEQUENCE: 40
cagccaatct tcattgctca                                              20

SEQ ID NO: 41             moltype = DNA   length = 20
FEATURE                   Location/Qualifiers
misc_feature              1..20
                          note = Primer
source                    1..20
```

```
                            mol_type = other DNA
                            organism = synthetic construct
SEQUENCE: 41
aggcagagag ggaaggagag                                                    20

SEQ ID NO: 42               moltype = DNA  length = 20
FEATURE                     Location/Qualifiers
misc_feature                1..20
                            note = Primer
source                      1..20
                            mol_type = other DNA
                            organism = synthetic construct
SEQUENCE: 42
taccccagg agaagattgt                                                     20

SEQ ID NO: 43               moltype = DNA  length = 20
FEATURE                     Location/Qualifiers
misc_feature                1..20
                            note = Primer
source                      1..20
                            mol_type = other DNA
                            organism = synthetic construct
SEQUENCE: 43
ttttctgcca gtgcctcttt                                                    20

SEQ ID NO: 44               moltype = DNA  length = 20
FEATURE                     Location/Qualifiers
misc_feature                1..20
                            note = Primer
source                      1..20
                            mol_type = other DNA
                            organism = synthetic construct
SEQUENCE: 44
tgggtgggtc aggtttgatg                                                    20

SEQ ID NO: 45               moltype = DNA  length = 20
FEATURE                     Location/Qualifiers
misc_feature                1..20
                            note = Primer
source                      1..20
                            mol_type = other DNA
                            organism = synthetic construct
SEQUENCE: 45
gcccagctgc tgaggagagt                                                    20

SEQ ID NO: 46               moltype = DNA  length = 20
FEATURE                     Location/Qualifiers
misc_feature                1..20
                            note = Primer
source                      1..20
                            mol_type = other DNA
                            organism = synthetic construct
SEQUENCE: 46
tgcaaaacca aaccacaaga                                                    20

SEQ ID NO: 47               moltype = DNA  length = 20
FEATURE                     Location/Qualifiers
misc_feature                1..20
                            note = Primer
source                      1..20
                            mol_type = other DNA
                            organism = synthetic construct
SEQUENCE: 47
tctcggagat ctcgaagcat                                                    20

SEQ ID NO: 48               moltype = DNA  length = 20
FEATURE                     Location/Qualifiers
misc_feature                1..20
                            note = Primer
source                      1..20
                            mol_type = other DNA
                            organism = synthetic construct
SEQUENCE: 48
tgggaatctc agatgggaag                                                    20

SEQ ID NO: 49               moltype = DNA  length = 20
FEATURE                     Location/Qualifiers
misc_feature                1..20
                            note = Primer
```

```
source                      1..20
                            mol_type = other DNA
                            organism = synthetic construct
SEQUENCE: 49
ctgtgtcccc cagaacttgt                                              20

SEQ ID NO: 50               moltype = DNA   length = 20
FEATURE                     Location/Qualifiers
misc_feature                1..20
                            note = Primer
source                      1..20
                            mol_type = other DNA
                            organism = synthetic construct
SEQUENCE: 50
actgagggga agggacaact                                              20

SEQ ID NO: 51               moltype = DNA   length = 20
FEATURE                     Location/Qualifiers
misc_feature                1..20
                            note = Primer
source                      1..20
                            mol_type = other DNA
                            organism = synthetic construct
SEQUENCE: 51
tcggtaccag gtgagggtag                                              20

SEQ ID NO: 52               moltype = DNA   length = 20
FEATURE                     Location/Qualifiers
misc_feature                1..20
                            note = Primer
source                      1..20
                            mol_type = other DNA
                            organism = synthetic construct
SEQUENCE: 52
cctcattgtc cagtgtggtg                                              20

SEQ ID NO: 53               moltype = DNA   length = 20
FEATURE                     Location/Qualifiers
misc_feature                1..20
                            note = Primer
source                      1..20
                            mol_type = other DNA
                            organism = synthetic construct
SEQUENCE: 53
tcttccgtct cgtcaggact                                              20

SEQ ID NO: 54               moltype = DNA   length = 20
FEATURE                     Location/Qualifiers
misc_feature                1..20
                            note = Primer
source                      1..20
                            mol_type = other DNA
                            organism = synthetic construct
SEQUENCE: 54
actgcttgga ggaccagaga                                              20

SEQ ID NO: 55               moltype = DNA   length = 20
FEATURE                     Location/Qualifiers
misc_feature                1..20
                            note = Primer
source                      1..20
                            mol_type = other DNA
                            organism = synthetic construct
SEQUENCE: 55
ggaaagcatt agcaggcaag                                              20

SEQ ID NO: 56               moltype = DNA   length = 20
FEATURE                     Location/Qualifiers
misc_feature                1..20
                            note = Primer
source                      1..20
                            mol_type = other DNA
                            organism = synthetic construct
SEQUENCE: 56
ggcggtgacc tcacaagtat                                              20

SEQ ID NO: 57               moltype = DNA   length = 20
FEATURE                     Location/Qualifiers
misc_feature                1..20
```

```
                            note = Primer
source                      1..20
                            mol_type = other DNA
                            organism = synthetic construct
SEQUENCE: 57
acgaagccat ttggtaaacg                                                    20

SEQ ID NO: 58               moltype = DNA   length = 20
FEATURE                     Location/Qualifiers
misc_feature                1..20
                            note = Primer
source                      1..20
                            mol_type = other DNA
                            organism = synthetic construct
SEQUENCE: 58
catgtgagtc cctgtgatgg                                                    20

SEQ ID NO: 59               moltype = DNA   length = 20
FEATURE                     Location/Qualifiers
misc_feature                1..20
                            note = Primer
source                      1..20
                            mol_type = other DNA
                            organism = synthetic construct
SEQUENCE: 59
gactgcagca aagacatcca                                                    20

SEQ ID NO: 60               moltype = DNA   length = 20
FEATURE                     Location/Qualifiers
misc_feature                1..20
                            note = Primer
source                      1..20
                            mol_type = other DNA
                            organism = synthetic construct
SEQUENCE: 60
gctgtgcagg agatcacaga                                                    20

SEQ ID NO: 61               moltype = DNA   length = 20
FEATURE                     Location/Qualifiers
misc_feature                1..20
                            note = Primer
source                      1..20
                            mol_type = other DNA
                            organism = synthetic construct
SEQUENCE: 61
gggctccata aagtcaccaa                                                    20

SEQ ID NO: 62               moltype = DNA   length = 20
FEATURE                     Location/Qualifiers
misc_feature                1..20
                            note = Primer
source                      1..20
                            mol_type = other DNA
                            organism = synthetic construct
SEQUENCE: 62
tccttcagac accctcaacc                                                    20

SEQ ID NO: 63               moltype = DNA   length = 20
FEATURE                     Location/Qualifiers
misc_feature                1..20
                            note = Primer
source                      1..20
                            mol_type = other DNA
                            organism = synthetic construct
SEQUENCE: 63
aggccccagt ttgaattctt                                                    20
```